(12) United States Patent
Kelly et al.

(10) Patent No.: US 11,714,058 B2
(45) Date of Patent: Aug. 1, 2023

(54) SYSTEMS AND METHODS FOR ANALYTE SENSING IN PHYSIOLOGICAL GAS SAMPLES

(71) Applicant: Boston Scientific Scimed, Inc., Maple Grove, MN (US)

(72) Inventors: David W. Kelly, Eagan, MN (US); Gregory J. Sherwood, North Oaks, MN (US); Justin Theodore Nelson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/101,900

(22) Filed: Nov. 23, 2020

(65) Prior Publication Data

US 2021/0148848 A1    May 20, 2021

Related U.S. Application Data

(63) Continuation of application No. 16/037,218, filed on Jul. 17, 2018, now Pat. No. 10,852,264.

(60) Provisional application No. 62/533,916, filed on Jul. 18, 2017.

(51) Int. Cl.
*G01N 27/22* (2006.01)

(52) U.S. Cl.
CPC ......... *G01N 27/227* (2013.01); *G01N 27/226* (2013.01)

(58) Field of Classification Search
CPC ... G01N 27/227; G01N 27/226; G01N 33/497

USPC ........................................................ 324/672
See application file for complete search history.

(56) References Cited

U.S. PATENT DOCUMENTS

| | | |
|---|---|---|
| 3,661,528 A | 5/1972 | Falk |
| 3,952,730 A | 4/1976 | Key |
| 3,981,297 A | 9/1976 | Dunn et al. |
| 4,820,011 A | 4/1989 | Umegaki et al. |
| 4,901,727 A | 2/1990 | Goodwin |

(Continued)

FOREIGN PATENT DOCUMENTS

| | | |
|---|---|---|
| CN | 1301342 | 6/2001 |
| CN | 102183557 | 9/2011 |

(Continued)

OTHER PUBLICATIONS

"Extended European Search Report," for European Patent Application No. 20214733.6 dated Apr. 21, 2021 (11 pages).

(Continued)

*Primary Examiner* — Farhana A Hoque
(74) *Attorney, Agent, or Firm* — Pauly, DeVries Smith & Deffner LLC

(57) ABSTRACT

Embodiments herein relate to systems and devices for measuring analyte presence on graphene varactors, which can be used for analyte sensing in physiological gas samples. In an embodiment, a system for measuring analyte presence on a graphene varactor is included having a capacitance to digital converter (CDC) and a graphene varactor. The CDC can be in electrical communication with the graphene varactor and can be configured to measure the capacitance of the graphene varactor in response to an excitation signal over a plurality of DC bias voltages. Other embodiments are also included herein.

19 Claims, 10 Drawing Sheets

(56) References Cited

U.S. PATENT DOCUMENTS

| | | |
|---|---|---|
| 5,174,290 A | 12/1992 | Fiddian-Green |
| 5,186,172 A | 2/1993 | Fiddian-Green |
| 5,357,971 A | 10/1994 | Sheehan et al. |
| 5,423,320 A | 6/1995 | Salzman et al. |
| 5,704,368 A | 1/1998 | Asano et al. |
| 5,834,626 A | 11/1998 | De Castro et al. |
| 5,928,155 A | 7/1999 | Eggers et al. |
| 6,006,121 A | 12/1999 | Vantrappen et al. |
| 6,029,076 A | 2/2000 | Fiddian-Greene et al. |
| 6,085,576 A * | 7/2000 | Sunshine ............ G01N 33/0031 73/29.01 |
| 6,149,624 A | 11/2000 | McShane |
| 6,170,318 B1 | 1/2001 | Lewis |
| 6,192,168 B1 | 2/2001 | Feldstein et al. |
| 6,238,339 B1 | 5/2001 | Fiddian-Greene et al. |
| 6,248,078 B1 | 6/2001 | Risby et al. |
| 6,312,390 B1 | 11/2001 | Phillips et al. |
| 6,480,734 B1 | 11/2002 | Zhang et al. |
| 6,599,253 B1 | 7/2003 | Baum et al. |
| 6,615,066 B2 | 9/2003 | Huyberechts et al. |
| 6,712,770 B2 | 3/2004 | Lin et al. |
| 6,726,637 B2 | 4/2004 | Phillips et al. |
| 6,733,464 B2 | 5/2004 | Olbrich et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,955,562 B2 | 6/2011 | Hong et al. |
| 7,972,277 B2 | 7/2011 | Oki et al. |
| 7,988,917 B2 | 8/2011 | Roesicke et al. |
| 7,992,422 B2 | 8/2011 | Leddy et al. |
| 8,043,860 B2 | 10/2011 | Leznoff et al. |
| 8,052,933 B2 | 11/2011 | Schirmer et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,244,355 B2 | 8/2012 | Bennett et al. |
| 8,294,135 B2 | 10/2012 | Lebedev et al. |
| 8,366,630 B2 | 2/2013 | Haick et al. |
| 8,479,731 B2 | 7/2013 | Heinonen et al. |
| 8,481,324 B2 | 7/2013 | Nakhoul et al. |
| 8,494,606 B2 | 7/2013 | Debreczeny et al. |
| 8,529,459 B2 | 9/2013 | Stahl et al. |
| 8,581,262 B2 | 11/2013 | Pan et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,951,473 B2 | 2/2015 | Wang et al. |
| 8,955,367 B2 | 2/2015 | Gouma et al. |
| 8,961,830 B2 | 2/2015 | Reynolds et al. |
| 9,011,779 B1 | 4/2015 | Anglin, Jr. et al. |
| 9,029,168 B2 | 5/2015 | Mannoor et al. |
| 9,034,170 B2 | 5/2015 | Blackburn et al. |
| 9,085,715 B2 | 7/2015 | Berthelot et al. |
| 9,103,775 B2 | 8/2015 | Bradley et al. |
| 9,138,169 B2 | 9/2015 | Beard |
| 9,147,398 B2 | 9/2015 | White et al. |
| 9,147,851 B1 | 9/2015 | Bartsch et al. |
| 9,267,908 B2 | 2/2016 | Wang et al. |
| 9,299,238 B1 | 3/2016 | Ahmad et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,528,979 B2 | 12/2016 | Haick et al. |
| 9,618,476 B2 | 4/2017 | Goldsmith |
| 9,638,169 B2 | 5/2017 | Obrecht |
| 9,642,577 B1 | 5/2017 | Li et al. |
| 9,671,392 B2 | 6/2017 | Jeppsen et al. |
| 9,689,836 B2 | 6/2017 | Makaram et al. |
| 9,696,311 B2 | 7/2017 | Haick et al. |
| 9,763,600 B2 | 9/2017 | Van Kesteren et al. |
| 9,765,395 B2 | 9/2017 | Goldsmith |
| 9,775,241 B2 | 9/2017 | Walczak et al. |
| 9,859,034 B2 | 1/2018 | Sjong |
| 9,936,897 B2 | 4/2018 | Carlson et al. |
| 9,977,011 B2 | 5/2018 | Beck et al. |
| 10,034,621 B2 | 7/2018 | Wondka et al. |
| 10,046,323 B2 | 8/2018 | Bos |
| 10,307,080 B2 | 6/2019 | Ssenyange et al. |
| 10,493,276 B2 | 12/2019 | Moffitt et al. |
| 10,543,035 B2 | 1/2020 | Sutermeister et al. |
| 10,770,182 B2 | 9/2020 | Sherwood et al. |
| 10,852,264 B2 | 12/2020 | Kelly et al. |
| 11,079,371 B2 | 8/2021 | Zhen et al. |
| 11,085,921 B2 | 8/2021 | Livache et al. |
| 11,172,846 B2 | 11/2021 | Sherwood et al. |
| 11,191,457 B2 | 12/2021 | Sherwood et al. |
| 11,262,354 B2 | 3/2022 | Sherwood |
| 11,662,325 B2 | 5/2023 | Sherwood et al. |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2004/0039295 A1 | 2/2004 | Olbrich et al. |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2007/0265509 A1 | 11/2007 | Burch et al. |
| 2008/0021339 A1 | 1/2008 | Gabriel et al. |
| 2008/0038154 A1 | 2/2008 | Longbottom et al. |
| 2008/0052122 A1 | 2/2008 | Iliff |
| 2008/0146890 A1 | 6/2008 | LeBoeuf et al. |
| 2008/0161709 A1 | 7/2008 | Bradley |
| 2008/0183910 A1 | 7/2008 | Natoli et al. |
| 2008/0228098 A1 | 9/2008 | Popov et al. |
| 2008/0317636 A1 | 12/2008 | Brahim et al. |
| 2009/0054799 A1 | 2/2009 | Vrtis et al. |
| 2009/0104435 A1 | 4/2009 | Hutchison et al. |
| 2009/0112115 A1 | 4/2009 | Huang et al. |
| 2009/0230300 A1 | 9/2009 | Trevejo et al. |
| 2010/0024533 A1 | 2/2010 | Kimura et al. |
| 2010/0056892 A1 | 3/2010 | Ben-Barak et al. |
| 2010/0085067 A1 | 4/2010 | Gabriel et al. |
| 2010/0116021 A1 | 5/2010 | O'Brien |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0268479 A1 | 10/2010 | Potyrailo et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0059476 A1 | 3/2011 | Shin et al. |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok et al. |
| 2012/0100636 A1 | 4/2012 | Johal et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |

(56) References Cited

U.S. PATENT DOCUMENTS

| | | |
|---|---|---|
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0224761 A1 | 8/2013 | Imberty et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-Silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |
| 2014/0145735 A1* | 5/2014 | Koester ............ G01R 27/2605 324/686 |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0275854 A1 | 9/2014 | Venkatraman et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0164373 A1 | 6/2015 | Davis et al. |
| 2015/0196251 A1 | 7/2015 | Outwater et al. |
| 2015/0250408 A1 | 9/2015 | Ssenyange et al. |
| 2015/0257676 A1 | 9/2015 | Fries |
| 2015/0265184 A1 | 9/2015 | Wondka et al. |
| 2015/0295562 A1 | 10/2015 | Agarwal et al. |
| 2015/0298115 A1 | 10/2015 | Campidelli et al. |
| 2015/0301021 A1 | 10/2015 | Haick et al. |
| 2015/0307936 A1* | 10/2015 | Goldsmith ......... G01N 27/4145 506/38 |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0093806 A1 | 3/2016 | Turchanin |
| 2016/0109440 A1 | 4/2016 | Sherwood et al. |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0289769 A1 | 10/2016 | Schwartz et al. |
| 2016/0334381 A1 | 11/2016 | King-smith et al. |
| 2016/0334386 A1 | 11/2016 | Anglin et al. |
| 2016/0356741 A1 | 12/2016 | Makaram et al. |
| 2016/0370337 A1 | 12/2016 | Blackley |
| 2017/0014043 A1 | 1/2017 | McDonnell |
| 2017/0042435 A1 | 2/2017 | Vermeulen et al. |
| 2017/0053068 A1 | 2/2017 | Pillai et al. |
| 2017/0067888 A1 | 3/2017 | Taslim et al. |
| 2017/0082566 A1 | 3/2017 | Koester |
| 2017/0212116 A1 | 7/2017 | Braga et al. |
| 2017/0227491 A1 | 8/2017 | Johnson et al. |
| 2017/0307562 A1 | 10/2017 | Goldsmith |
| 2017/0307576 A1* | 10/2017 | Anglin, Jr. ......... G01N 33/0059 |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0035932 A1 | 2/2018 | Massova |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0328841 A1 | 11/2018 | Graham et al. |
| 2018/0336970 A1 | 11/2018 | Sherwood et al. |
| 2019/0025237 A1 | 1/2019 | Kelly et al. |
| 2019/0178837 A1 | 6/2019 | Xu et al. |
| 2019/0254538 A1 | 8/2019 | Erdman et al. |
| 2019/0257825 A1 | 8/2019 | Zhen et al. |
| 2019/0286866 A1 | 9/2019 | Gurt |
| 2019/0331661 A1 | 10/2019 | Zhen et al. |
| 2020/0166435 A1 | 5/2020 | Sherwood et al. |
| 2020/0191737 A1 | 6/2020 | Sherwood et al. |
| 2021/0057526 A1 | 2/2021 | Zhen et al. |
| 2021/0072208 A1 | 3/2021 | Sherwood et al. |
| 2021/0341409 A1 | 11/2021 | Rognrud et al. |
| 2022/0334075 A1 | 10/2022 | Koester et al. |

FOREIGN PATENT DOCUMENTS

| | | |
|---|---|---|
| CN | 102770069 | 11/2012 |
| CN | 102941042 | 2/2013 |
| CN | 103332678 | 10/2013 |
| CN | 103814294 | 5/2014 |
| CN | 103950920 | 7/2014 |
| CN | 104914138 | 9/2015 |
| CN | 103852505 | 11/2015 |
| CN | 103877574 | 1/2016 |
| CN | 105445335 | 3/2016 |
| CN | 105527321 | 4/2016 |
| CN | 105688995 | 6/2016 |
| CN | 106152924 | 11/2016 |
| CN | 107180706 | 9/2017 |
| CN | 109270130 | 1/2019 |
| CN | 109310326 | 2/2019 |
| CN | 109862829 | 6/2019 |
| CN | 110769742 | 2/2020 |
| CN | 107076693 | 9/2020 |
| EP | 1764153 | 3/2007 |
| EP | 1806414 | 7/2007 |
| EP | 3093653 | 11/2016 |
| EP | 3210007 | 8/2017 |
| EP | 3439544 | 2/2019 |
| EP | 3528703 | 8/2019 |
| EP | 3624678 | 3/2020 |
| EP | 3431977 | 12/2020 |
| IN | 201627028955 | 10/2016 |
| JP | H07507943 | 9/1995 |
| JP | H11174051 | 7/1999 |
| JP | 2005514081 | 5/2005 |
| JP | 2008516209 | 5/2008 |
| JP | 2009244074 | 10/2009 |
| JP | 2011102747 | 5/2011 |
| JP | 2011523363 | 8/2011 |
| JP | 2012122814 | 6/2012 |
| JP | 2012517276 | 8/2012 |
| JP | 2016022415 | 2/2016 |
| JP | 2016511456 | 4/2016 |
| JP | 2016122249 | 7/2016 |
| JP | 2017123912 | 7/2017 |
| JP | 2019020415 | 2/2019 |
| JP | 2019527365 | 9/2019 |
| JP | 2019536013 | 12/2019 |
| JP | 2020521128 | 7/2020 |

(56) References Cited

FOREIGN PATENT DOCUMENTS

| | | |
|---|---|---|
| KR | 20170057001 | 5/2017 |
| KR | 101797737 | 11/2017 |
| WO | 9325142 | 12/1993 |
| WO | 9947905 | 9/1999 |
| WO | 2001070114 | 9/2001 |
| WO | 2008083285 | 7/2008 |
| WO | 2008088780 | 7/2008 |
| WO | 2009020647 | 2/2009 |
| WO | 2009135070 | 11/2009 |
| WO | 2011109736 | 9/2011 |
| WO | 2012135565 | 10/2012 |
| WO | 2012145247 | 10/2012 |
| WO | 2013095730 | 6/2013 |
| WO | 2013189502 | 12/2013 |
| WO | 2014064740 | 5/2014 |
| WO | 2015134895 | 9/2015 |
| WO | 2015179623 | 11/2015 |
| WO | 2015191558 | 12/2015 |
| WO | 2016064740 | 4/2016 |
| WO | 2016105464 | 6/2016 |
| WO | 2016145300 | 9/2016 |
| WO | 2017066583 | 4/2017 |
| WO | 2017095922 | 6/2017 |
| WO | 2017218464 | 12/2017 |
| WO | 2018053932 | 3/2018 |
| WO | 2018075731 | 4/2018 |
| WO | 2018213564 | 11/2018 |
| WO | 2020102880 | 5/2020 |
| WO | 2020112825 | 6/2020 |
| WO | 2020131567 | 6/2020 |
| WO | 2021222489 | 11/2021 |

OTHER PUBLICATIONS

"Final Office Action," for U.S. Appl. No. 15/621,103 dated Apr. 22, 2021 (20 pages).
"Non-Final Office Action," for U.S. Appl. No. 14/883,895 dated May 20, 2021 (34 pages).
"Non-Final Office Action," for U.S. Appl. No. 15/787,985 dated Apr. 16, 2021 (16 pages).
Zhang, Xu et al., "A Wide Measurement Range and Fast Update Rate Integrated Interface for Capacitive Sensors Array," IEEE Transactions on Circuits and Systems -1: Regular Papers, Vo. 61, No. 1, Jan. 2014, pp. 2-11 (10 pages).
"International Preliminary Report on Patentability," for PCT Application No. PCT/US2019/063324 dated Jun. 10, 2021 (10 pages).
"Office Action," for Chinese Patent Application No. 201780065376.2 dated Apr. 27, 2021 (10 pages) with English Summary.
"Response to Final Rejection," dated Apr. 22, 2021 for U.S. Appl. No. 15/621,103, submitted via EFS-Web on Jun. 22, 2021, 13 pages.
"Response to Non-Final Rejection," dated Apr. 16, 2021 for U.S. Appl. No. 15/787,985, submitted via EFS-Web on Jun. 22, 2021, 11 pages.
"Second Office Action," for Chinese Patent Application No. 201780030595.7 dated Jun. 17, 2021 (8 pages), with English Summary.
Office Action for Japanese Patent Application No. 2019-520955 dated Feb. 9, 2021 (11 pages) with English Translation.
Response to Communication Pursuant to Article 94(3) EPC for European Patent Application No. 18731579.1 filed Mar. 15, 2021 (12 pages).
"International Preliminary Report on Patentability," for PCT Application No. PCT/US2019/065981 dated Jul. 1, 2021 (8 pages).
"International Search Report and Written Opinion," for PCT Application No. PCT/US2021/026778 dated Aug. 3, 2021 (11 pages).
"New Summons to Attend Oral Proceedings," for European Patent Application No. 18731579.1 dated Jul. 12, 2021 (6 pages).
"Notice of Allowance," for U.S. Appl. No. 15/621,103 dated Aug. 3, 2021 (18 pages).
"Notice of Allowance," for U.S. Appl. No. 15/787,985 dated Jul. 15, 2021 (14 pages).
"Response to Final Rejection," dated Apr. 22, 2021 and the Advisory Action dated Jul. 8, 2021 for U.S. Appl. No. 15/621,103, submitted via EFS-Web on Jul. 12, 2021, 13 pages.
"Summons to attend oral proceedings pursuant to Rule 115(1) EPC," for European Patent Application No. 18731579.1 dated Jul. 1, 2021 (6 pages).
Planz, B., et al. "The role of urinary cytology for detection of bladder cancer," EJSO (2005) 21, 304-308 (5 pages).
Ramakumar, Sanjay, et al. "Comparison of Screening Methods in the Detection of Bladder Cancer," The Journal of Urology vol. 161, 388-394, Feb. 1999 (7 pages).
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).
Bhadra, Sharmista et al., "Non-destructive detection of fish spoilage using a wireless basic volatile sensor," Talanta, vol. 134, Dec. 25, 2014 pp. 718-723 (6 pages).
Boots, Agnes W. et al., "The Versatile Use of Exhaled Volatile Organic Compounds in Human Health and Disease," J. Breath Res. 6 (2012) 027108 (21 pages).
Chamberlain li, Richard V. et al., "Electrostatically-induced Inclusion of Anions in Cyclodextrin Monolayers on Electrodes," Langmuir 2000, 1388-1396 (9 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Di Natale, Corrado et al., "Lung Cancer Identification by the Analysis of Breath by Means of an Array of Non-Selective Gas Sensors," Biosensors and Bioelectronics 18 (2003) 1209-1218 (10 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
Ebrish, M. A. et al., "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
"European Search Report," for Dutch Patent Application No. 2019492 dated Apr. 12, 2018 (10 pages).
"Fdc1004 4-Channel Capacitance-to-Digital Converter for Capacitive Sensing Solutions," Data Sheet SNOSCY5B Texas Instruments Aug. 2014—Revised 2015 (24 pages).
"Fdc1004evm User Guide," Literature No. SNAU163C, Texas Instruments August 2014—Revised Oct. 2016 (46 pages).
File History for European Patent Application No. 15790739.5 downloaded Jan. 26, 2021 (238 pages).
File History for European Patent Application No. 17733246.7 downloaded Jan. 26, 2021 (132 pages).
File History for European Patent Application No. 17794832.0 downloaded Jan. 26, 2021 (152 pages).
File History for European Patent Application No. 18731579.1 downloaded Jan. 26, 2021 (254 pages).
File History for European Patent Application No. 18180455.0 downloaded Jan. 26, 2021 (351 pages).
File History for U.S. Appl. No. 14/883,895 downloaded Jan. 26, 2021 (513 pages).
File History for U.S. Appl. No. 15/621,103 downloaded Jan. 26, 2021 (419 pages).
File History for U.S. Appl. No. 15/787,985 downloaded Jan. 26, 2021 (368 pages).
File History for U.S. Appl. No. 15/982,506 downloaded Jan. 26, 2021 (281 pages).
File History for U.S. Appl. No. 16/037,218 downloaded Jan. 26, 2021 (278 pages).
"First Office Action," for Chinese Patent Application No. 201580056417.2 dated Feb. 11, 2019 (13 pages) with English summary.

(56) References Cited

OTHER PUBLICATIONS

"First Office Action," for Chinese Patent Application No. 201780030595.7 dated Nov. 2, 2020 (12 pages) with English Summary.
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Georgakilas, Vasilios et al., "Noncovalent Functionalization of Graphene and Graphene Oxide for Energy Materials, Biosensing, Catalytic, and Biomedical Applications," Chem. Rev. 2016, 116, 5464-5519 (56 pages).
Guo, Yujing et al., "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).
"International Preliminary Report on Patentability," for PCT Application No. PCT/US2017/057318 dated May 2, 2019 (11 pages).
"International Preliminary Report on Patentability," for PCT Application No. PCT/US2018/033166 dated Nov. 28, 2019 (8 pages).
"International Preliminary Report on Patentability," for PCT Application No. PCT/US2018/037144 dated Dec. 27, 2018 (7 pages).
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).
"International Search Report and Written Opinion," for PCT Application No. PCT/US2017/057318 dated Feb. 6, 2018 (14 pages).
"International Search Report and Written Opinion," for PCT Application No. PCT/US2018/033166 dated Oct. 2, 2018 (12 pages).
"International Search Report and Written Opinion," for PCT Application No. PCT/US2019/063324 dated Mar. 27, 2020 (17 pages).
"International Search Report and Written Opinion," for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).
Ma, Rui et al., "Acetone Sensing Using Graphene Quantum Capacitance Varactors," 2016 IEEE Sensors, Orlando, FL, 2016 (3 pages).
Machado, Roberto F. et al., "Detection of Lung Cancer by Sensor Array Analyses of Exhaled Breath," Am J Respir Crit Care Med, vol. 171, 1286-1291 (2005), 6 pages.
"Mechanical Data," DGS (S-PDSO-G10) DSC0010B Package Outline, Example Board Layout, and Stencil Design. Texas Instruments 2016 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.reuters.com/finance/stocks/companyProfile?symbol=VNTH.PK> accessed Mar. 17, 2017 (2 pages).
Navaneethan, Udayakumar et al., "Volatile Organic Compounds in Bile Can Diagnose Malignant Biliary Strictures in the Setting of Pancreatic Cancer: a Preliminary Observation," Gastrointest Endosc. Dec. 2014;80(6):1038-45 (8 pages).
"Office Action," for Japanese Patent Application No. 2019-517196 dated Feb. 4, 2020 (10 pages) with English Translation.
"Office Action," for Japanese Patent Application No. 2019-520955 dated Jul. 14, 2020 (10 pages) with English Translation.
"Office Action," for Japanese Patent Application No. 2019-563876 dated Nov. 4, 2020 (5 pages) with English Summary.
Olson, Eric J. et al., "Capacitive Sensing of Intercalated H2O Molecules Using Graphene," ACS Appl. Mater. Interfaces 2015, 7(46), 25804-25812 (29 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
Putta, Chandrababu et al., "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
Rojas, Maria T. et al., "Supported Monolayers Containing Preformed Binding-Sites—Synthesis and Interfacial Binding-Properties of a Thiolated Beta-Cyclodextrin Derivative," J. Am. Chem. Soc. 1995, 117, 336-343 (8 pages).
"Second Office Action," for Chinese Patent Application No. 201580056417.2 dated Sep. 25, 2019 (8 pages) with English Summary.
"Standard Terms and Conditions for Evaluation Modules," Texas Instruments 2016 (5 pages).
"Third Office Action," for Chinese Patent Application No. 201580056417.2 dated Feb. 18, 2020 (9 pages) with English Summary.
Tripathi, Kumud M et al., "Recent Advances in Engineered Graphene and Composites for Detection of Volatile Organic Compounds (VOCs) and Non-Invasive Diseases Diagnosis," Carbon 110 (2016)97-129 (34 pages).
Wang, David "FDC1004: Basics of Capacitive Sensing and Applications," Application Report SNOA927, Texas Instruments Dec. 2014 (12 pages).
Wayu, Mulugeta B. et al., "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, SENSORS 2016—Proceedings, Orlando, FL 2016 (3 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
"First Office Action," for Chinese Patent Application No. 201880032911.9 dated Nov. 3, 2021 (11 pages) with English Summary.
"Notice of Allowance," for U.S. Appl. No. 14/883,895 dated Oct. 22, 2021 (18 pages).
"Response to Communication Pursuant to Rules 161(1) and 162 EPC," for European Patent Application No. 19828373.1 filed Nov. 8, 2021 (22 pages).
"Response to Communication Pursuant to Rules 70(2) and 70a(2)/Rule 39(1)," for European Patent Application No. 20214733.6 filed Nov. 23, 2021 (4 pages).
"Second Office Action," for Chinese Patent Application No. 201780065376.2 dated Nov. 16, 2021 (8 pages) with English Summary.
"Written Submission," in Response to Summons to Attend Oral Proceedings for European Patent Application No. 18731579.1 filed Nov. 30, 2021 (31 pages).

(56) References Cited

OTHER PUBLICATIONS

Groves, William A., et al. "Analysis of Solvent Vapors in Breath and Ambient Air with a Surface Acoustic Wave Sensor Array," Ann. Occup. Hyg., vol. 45, No. 8, pp. 609-623, 2001 (15 pages).
"Communication Pursuant to Article 94(3) EPC," for European Patent Application No. 17733246.7 dated Jan. 28, 2022 (6 pages).
"Communication Pursuant to Article 94(3) EPC," for European Patent Application No. 17794832.0 dated Mar. 7, 2022 (9 pages).
"First Office Action," for Chinese Patent Application No. 201810782878.3 dated Feb. 9, 2022 (14 pages) with English Summary.
"Office Action," for Japanese Patent Application No. 2018-133996 dated Jan. 25, 2022 (7 pages) with English Translation.
"Response to Communication Pursuant to Rules 161(1) and 162 EPC," for European Patent Application No. 19836341.8 filed Jan. 7, 2022 (12 pages).
"Communication Pursuant to Article 94(3) EPC," for European Patent Application No. 15790739.5 dated Jun. 3, 2022 (5 pages).
"Decision of Rejection," for Chinese Patent Application No. 201780065376.2 dated Apr. 1, 2022 (9 pages) with English Translation.
"Non-Final Office Action," for U.S. Appl. No. 16/696,348 dated Jun. 20, 2022 (68 pages).
"Non-Final Office Action," for U.S. Appl. No. 16/712,255 dated Jun. 23, 2022 (64 pages).
"Response to Communication Pursuant to Article 94(3) EPC," for European Patent Application No. 17733246.7 filed May 18, 2022 (9 pages).
"Communication Pursuant to Article 94(3) EPC," for European Patent Application No. 20214733.6 dated Jan. 16, 2023 (5 pages).
"International Preliminary Report on Patentability," for PCT Application No. PCT/US2021/026778 dated Nov. 10, 2022 (7 pages).
"Notice of Allowance," for U.S. Appl. No. 16/712,255 dated Jan. 20, 2023 (31 pages).
"Determination of Carbonyl Compounds by High performance Liquid Chromatography (HPLC)," EPA Method 8315A 1996 (34 pages).
"Final Office Action," for U.S. Appl. No. 16/696,348 dated Nov. 3, 2022 (39 pages).
"First Examination Report," for Australian Patent Application No. 2019224011 dated Apr. 9, 2021 (4 pages).
"International Preliminary Report on Patentability," for PCT Application No. PCT/US2019/018741 dated Sep. 3, 2020 (11 pages).
"International Preliminary Report on Patentability," for PCT Application No. PCT/US2019/028870 dated Nov. 5, 2020 (11 pages).
"International Search Report and Written Opinion," for PCT Application No. PCT/US2019/018741 dated May 6, 2019 (17 pages).
"International Search Report and Written Opinion," for PCT Application No. PCT/US2019/028870 dated Aug. 20, 2019 (17 pages).
"International Search Report and Written Opinion," for PCT Application No. PCT/US2020/046829 dated Nov. 18, 2020 (15 pages).
"International Search Report and Written Opinion," for PCT Application No. PCT/US2022/025004 dated Jul. 25, 2022 (15 pages).
"Non-Final Office Action," for U.S. Appl. No. 16/280,635 dated Feb. 10, 2021 (40 pages),.
"Non-Final Office Action," for U.S. Appl. No. 16/393,177 dated May 25, 2021 (37 pages).
"Notice of Allowance," for U.S. Appl. No. 16/280,635 dated Mar. 31, 2021 (14 pages).
"Office Action," for Japanese Patent Application No. 2018-133996 dated Jul. 12, 2022 (4 pages) with English Translation.
"Response to Communication Pursuant to Article 94(3) EPC," for European Patent Application No. 15790739.5 filed Oct. 12, 2022 (35 pages).
"Response to Communication Pursuant to Article 94(3) EPC," for European Patent Application No. 17794832.0 filed Jul. 7, 2022 (8 pages).
"Response to Communication Pursuant to Rules 161(1) and 162 EPC," for European Patent Application No. 19709268.7 filed Apr. 1, 2021 (12 pages).
"Response to Communication Pursuant to Rules 161(1) and 162 EPC," for European Patent Application No. 19733177.0 filed Jun. 4, 2021 (20 pages).
"Response to Examination Report," for Australian Patent Application No. 2019224011 filed Jul. 23, 2021 (22 pages).
"Response to Non-Final Rejection," dated Feb. 10, 2021 for U.S. Appl. No. 16/280,635, submitted via EFS-Web on Mar. 17, 2021, 16 pages.
"Response to Non-Final Rejection," dated Jun. 20, 2022 for U.S. Appl. No. 16/696,348, submitted via EFS-Web on Sep. 20, 2022, 9 pages.
"Response to Non-Final Rejection," dated Jun. 23, 2022 for U.S. Appl. No. 16/712,255, submitted via EFS-Web on Sep. 22, 2022, 7 pages.
"Response to Non-Final Rejection," dated May 20, 2021 for U.S. Appl. No. 14/883,895, submitted via EFS-Web on Aug. 19, 2021, 12 pages.
Agbonlahor, Osazuwa, et al."Adsorbed Molecules as Interchangeable Dopants and Scatterers with a van der Waals Bonding Memory in Graphene Sensors," ACS Sens. 2020, 5 (7), 2003-2009 (13 pages).
Allen, Matthew J., et al."Honeycomb Carbon: A Review of Graphene," Chem. Rev. 2010, 110, 132-145 (14 pages).
An, Xiaohong, et al."Stable Aqueous Dispersions of Noncovalently Functionalized Graphene from Graphite and their Multifunctional High-Performance Applications," Nano Lett. 2010, 10, 4295-4301 (7 pages).
Bair, Kenneth W., et al."(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J., et al."Electrochemical Methods: Fundamentals and Applications," Wiley New York: 1980; vol. 2 (850 pages).
Bartosik, Miroslav, et al."The mechanism and suppression of physisorbed-water caused hysteresis in graphene FET sensors," ACS Sens., vol. 5, 2940-2949 (2020). (40 pages).
Biedermann, Frank, et al."Experimental Binding Energies in Supramolecular Complexes," Chem. Rev. 2016, 116(9), 5216-5300 (85 pages).
Bock, Harald, et al."Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Brust, Mathias, et al."Novel Gold-Dithiol Nano-Networks with Non-Metallic Electronic Properties," Adv. Mater. 1995, 7, No. 9 795-797 (3 pages).
Brust, Mathias, et al."Synthesis of Thiol-derivatised Gold Nanoparticles in a Two-phase Liquid-Liquid System," J. Chem. Soc., Chem. Commun., 1994, 801-802 (2 pages).
Cancilla, Devon A., et al."O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).
Cao, Mengmei, et al."Electrochemical and Theoretical Study of $\pi$-$\pi$ stacking Interactions between Graphitic Surfaces and Pyrene Derivatives," J. Phys. Chem. C 2014, 118(5), 2650-2659 (10 pages).
Capuano, Rosamaria, et al."Corroles-Porphyrins: A Teamwork for Gas Sensor Arrays," Sensors, 2015, vol. 15, pp. 8121-8130 (10 pages).
Chen, Gugang, et al."Sub-ppt gas detection with pristine graphene," Applied Physics Letters 101, 053119 (2012) 6 pages.
Cheng, Zengguang, et al."Suspended Graphene Sensors with Improved Signal and Reduced Noise," Nano Lett. 2010, 10, 1864-1868 (5 pages).
Connors, Kenneth A., et al."The Stability of Cyclodextrin Complexes in Solution," Chem. Rev. 1997, 97, 1325-1357 (34 pages).
Cui, Menghua, et al."Graphene-organic two-dimensional charge transfer complexes: inter-molecular electronic transitions and broadband near infrared photoresponse," J. Phys. Chem. C 2018, 122 (13), 7551-7556 (7 pages).
Dreyer, Daniel, et al."The chemistry of graphene oxide," Chem. Soc. Rev. 2010, 39(1), 228-240 (13 pages).

(56) References Cited

OTHER PUBLICATIONS

Elemans, Johannes A.A.W., et al."Molecular Materials by Self-Assembly of Porphyrins, Phthalocyanines, and Perylenes," Adv. Mater. 2006, 18, 1251-1266 (16 pages).
Fan, Xuge, et al."Humidity and CO2 gas sensing properties of double-layer graphene," Carbon 127 (2018) 576-587 (12 pages).
Fogel, Yulia, et al."Graphitic Nanoribons with Dibenzo[e,l]pyrene Repeat Units: Synthesis and Self-Assembly," Macromolecules 2009, 42, 6878-6884 (7 pages).
Fuchs, Patricia, et al."Breath gas aldehydes as biomarkers of lung cancer," Int. J. Cancer 2010, 126 (11), 2663-70 (8 pages).
Gao, Zhaoli, et al."Scalable Production of Sensor Arrays Based on High-Mobility Hybrid Graphene Field Effect Transistors," ACS Applied Materials & Interfac. 2016, 8(41), 27546-27552 (8 pages).
Gautam, Madhav, et al."Gas sensing properites of graphene synthesized by chemical vapor deposition," Materials and Science Engineering C31 (2011) 1405-1411 (7 pages).
Gavartin, J.L., et al."The role of nitrogen-related defects in high-k dialectric oxides: Density-functional studies.," Journal of Applied Physics. vol. 97, Issue 5 (2005). (15 pages).
Geim, A.K., et al."The rise of graphene," Nat. Mater. 2007, 6, 183-191 (9 pages).
Georgakilas, Vasilios, et al."Functionalization of Graphene: Covalent and Non-Covalent Approaches, Derivatives and Applications," Chem. Rev. 2012, 112(11), 6156-6214 (59 pages).
Ghosh, Sujoy, et al."Effect of 1-Pyrene Carboxylic-Acid Functionalization of Graphene on Its Capacitive Energy Storage," J. Phys. Chem. C 2012, 116, 20688-20693 (6 pages).
Giancane, Gabriele, et al."State of Art in Porphyrin Langmuir-Blodgett Films as Chemical Sensors," Advances in Colloid and Interface Science, 2012, vol. 171-172, pp. 17-35 (Year: 2012), 19 pages.
Good, Robert J."Contact angle, wetting, and adhesion: a critical review," J. Adhesion Sci. Technol. 1992, vol. 6, No. 12, pp. 1269-1302 (34 pages).
Gorodetsky, Alon A., et al."Electrochemistry Using Self-assembled DNA Monolayers on Highly Oriented Pyrolytic Graphite," Langmuir 2006, 22, 7917-7922 (6 pages).
Guo, Zanru, et al."Light-Switchable Single-Walled Carbon Nanotubes Based on Host-Guest Chemistry," Adv. Funct. Mater. 2013, 23, 5010-5018 (18 pages).
Hasobe, Taku "Photo- and Electro-Functional Self-Assembled Architectures of Porphyrins," Physics Chemistry Chemical Physics, 2012, 14, pp. 15975-15987 (Year: 2012), 13 pages.
Hayasaka, Takeshi, et al."The influences of temperature, humidity, and O2 on electrical properties of graphene FETs," Sensors & Actuators: B. Chemical 285 (2019) 116-122 (7 pages).
Hill, Ernie W., et al."Graphene Sensors," IEEE Sensors Journal, vol. 11, No. 12, Dec. 2011 (10 pages).
Hinnemo, Malkolm, et al."On Monolayer Formation of Pyrenebutyric Acid on Graphene," Langmuir, 2017, vol. 33, No. 14 pp. 3588-3593 (6 pages).
Hockstein, Neil G., et al."Diagnosis of Pneumonia with an Electronic Nose: Correlation of Vapor Signature with Chest Computed Tomography Scan Findings," The Laryngoscope 2004, 114 (10), 1701-1705 (5 pages).
Hong Chan, Wing, et al."Optodes based on a calixarene ester for the determination of aldehydes via in situ generation of the Girard's reagent P derivative," Analyst 1998, 123 (12), 2851-2856 (6 pages).
Hsiao, Min-Chien, et al."Preparation and properties of a graphene reinforced nanocomposite conducting plate," J. Mater. Chem., 2010, 20, 8496-8505 (10 pages).
Hsieh, Chien-Te, et al."Field emission from various CuO nanostructures," Applied Physics Letters 2003, vol. 83, No. 6 (3 pages).
Huang, Ke-Jing, et al."Novel electrochemical sensor based on functionalized graphene for simultaneous determination of adenine and guanine in DNA," Colloids and Surfaces B: Biointerfaces 82 (2011) 543-549 (7 pages).
Hunter, Christopher A., et al."The Nature of π-π Interactions," J. Am. Chem. Soc. 1990, 112, 5525-5534 (10 pages).
Hwang, Michael, et al."Ultrasensitive detection of nucleic acids using deformed graphene channel field effect biosensors," Nat. Commun. 2020, 11(1) (11 pages).
Tezhokin, I., et al."Porphyrin molecules boost the sensitivity of epitaxial graphene for NH3 detection," J. Phy.: Condens. Matter 29 (2017) (11 pages).
Ionescu, Radu, et al."Detection of Multiple Sclerosis from exhaled Breath Using Bilayers of Polycyclic Aromatic Hydrocarbons and Single-Wall Carbon Nanotubes," ACS Chemical Neurosci. 2011, 2(12), 687-693 (7 pages).
Jiao, Dezhi, et al."Supramolecular Peptide Amphiphile Vesicles through Host-Guest Complexation," Angew. Chem. Int. Ed. 2012, 51, 9633-9637 (5 pages).
Kang, Junmo, et al."Graphene Transfer: key for applications," Nanoscale, 2012, 4, 5527 (11 pages).
Kang, Xinhuang, et al."Glucose Oxidase-graphene-chitosan modified electrode for direct electrochemistry and glucose sensing," Biosensors and Bioelectronics 25 (2009) 901-905 (5 pages).
Knipp, Ralph J., et al."A versatile probe for chemoselective capture and analysis of carbonyl compounds in exhaled breath," Anal Methods, 2015, 7, 6027 (7 pages).
Kobayashi, Keiko, et al."Gas chromatrographic determination of low-molecular-weight carbonyl compounds in aqueous solution as their O-(2,3,4,5,6-pentafluorobenzyl) oximes," Journal of Chromatography A 1980, 187(2), 413-417 (5 pages).
Kozbial, Andrew, et al."Study on the surface energy of graphene by contact angle measurement," Langmuir 2014, 30 (28), 8598-8606 (28 pages).
Kuila, Tapas, et al."Chemical functionalization of graphene and its applications," Progress in Materials Science 57 (2012) 1061-1105 (45 pages).
Lauffer, Peter, et al."Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph, et al."Adhesive Forces Between Aromatic Molecules and Graphene," The Journal of Physical Chemistry C 2014, 118(36), 20970-20981 (12 pages).
Lecourt, Thomas, et al."Triisobutylaluminium and Diisobutylaluminium Hydride as Molecular Scalpels: the Regioselective Stripping of Perbenzylate Sugars and Cyclodextrins," Chem. Eur. J. 2004, 10, 2960-2971 (12 pages).
Li, Errui, et al."Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).
Li, Mingxiao, et al."Preconcentration and Analysis of Trace Volatile Carbonyl Compounds," Anal Chem 2012, 84(3), 1288-1293 (6 pages).
Lienerth, Peter, et al."Improving the Selectivity to Polar Vapors of OFET-Based Sensors by Using the Tranfser Charactersitics Hysteresis Response," Sensors and Actuators B 225 (2016) 90-95 (6 pages).
Liu, Sophie F., et al."Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).
Liu, Yifei M., et al."Electrochemical Sensing of Nitric Oxide with Functionalized Graphene Electrodes," ACS Applied Materials & Interfaces 2013, 5(23), 12624-12630 (7 pages).
Liu, Yuxin, et al."Biological and Chemical Sensors based on Graphene Materials," Chem. Soc. Rev. 2012, 41 (6), 2283-2307 (27 pages).
Loh, Kian Ping, et al."The Chemistry of Graphene," J. Mater. Chem., 2010, 20, 2277-2289 (13 pages).
Long, Brenda, et al."Non-Covalent Functionalization of Graphene Using Self-Assembly of Alkane-Amines," Adv. Funct. Mater. 2012, 22, 717-725 (9 pages).
Lu, Chun-Hua, et al."A Graphene Platform for Sensing Biomolecules," Angew. Chem. Int. Ed. 2009, 48, 4785-4787 (3 pages).

(56) References Cited

OTHER PUBLICATIONS

Mackin, Charles, et al."Chemiresistive Graphene Sensors for Ammonia Detection," ACS Appl. Mater. Interfaces 2018, 10, 16169-16176 (8 pages).
Mann, Jason A., et al."Improving the Binding Characteristics of Tripodal Compounds on Single Layer Graphene," American Chemical Society 2013, vol. 7, No. 8, 7193-7199 (7 pages).
Manochehry, Sepehr, et al."Optical biosensors utilizing graphene and functional DNA molecules," J. Mater. Res. 2017, 32(15), 2973-2983 (11 pages).
Manolis, Antony "The Diagnostic Potential of Breath Analysis," Clin. Chem. 29/1, 5-15 (1983) (11 pages).
Mao, Shun, et al."Specific Protein Detection Using Thermally Reduced Graphene Oxide Sheet Decorated with Gold Nanoparticle-Antibody Conjugates," Adv. Mater. 2010, 22, 3521-3526 (6 pages).
McCulloch, Michael, et al."Diagnostic Accuracy of Canine Scent Detection in Early-and Late-Stage Lung and Breast Cancers," Integrative Cancer Therapies 2006, 5(1), 30-39 (11 pages).
Moldoveanu, Serban C., et al."Derivatization Methods in GC and GC/MS," in Gas Chromatography-Derivatization, Sample Preparation, Application, Kusch, P., Ed. IntechOpen:2018 (33 pages).
Muruganathan, Manoharan, et al."Electrically Tunable van der Waals Interaction in Graphene—Molecule Complex," Nano Lett. 2015, 15(12), 8176-8180 (5 pages).
Nag, Sanada, et al."Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).
Novoselov, K.S., et al."Electric Field Effect in Atomically Thin Carbon Films," Science 2004, 306, 666-669 (5 pages).
Ohno, Yasuhide, et al."Electrolyte-Gated Graphene Field-Effect Transistors for Detecting pH and Protein Adsorption," Nano Letters 2009, vol. 9, No. 9, 3318-3322 (5 pages).
Olson, Eric J., et al."Getting More out of a Job Plot: Determination of Reactant to Product Stoichiometry in Cases of Displacement Reactions and n:n Complex Formation," J. Org. Chem. 2011, 76, 8406-8412 (7 pages).
Ou, Baoli, et al."Covalent functionalization of graphene with poly(methyl methacrylate) by atom transfer radical polymerization at room temperature," Polym. Chem., 2012, 3, 2768 (8 pages).
Park, Eun Uk, et al."Correlation between the sensitivity and the hysteresis of humidity sensors based on graphene oxides," Sensors and Actuators B 258 (2018) 255-262 (8 pages).
Pathipati, Srinivasa Rao, et al."Modulation of charge transport properties of reduced graphene oxide by submonolayer physisorption of an organic dye," Organic Electronics 14 (2013) 1787-1792 (6 pages).
Peng, Gang, et al."Diagnosing lung cancer in exhaled breath using gold nanoparticles," Nature nanotechnology, 2009, 4(10), 669-673 (5 pages).
Peressi, Maria "Surface Functionalization of Graphene," Graphene Chemistry, John Wiley & Sons, Ltd:2013, pp. 233-253 (21 pages).
Poli, Diana, et al."Determination of aldehydes in exhaled breath of patients with lung cancer by means of on-fiber-derivatisation SPME-GC/MS," Journal of Chromatography B, 878 (2010) 2643- 2651 (9 pages).
Poulston, S., et al."Surface Oxidation and Reduction of CuO and Cu2O Studied Using XPS and XAES," Surface and Interface Analysis, vol. 24, 811-820, 1996, (10 pages).
Pyo, Soonjae, et al."Improved photo- and chemical-responses of graphene via porphyrin-functionalization for flexible, transparent, and sensitive sensors," Nanotechnology 30 (2019) 215501 (9 pages).
Rekharsky, Mikhail V., et al."Complexation Thermodynamics of Cyclodextrins," Chem. Rev. 1998, 98, 1875-1917 (44 pages).
Reuillard, B., et al."Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).

Rodner, Marius, et al."Graphene Decorated with Iron Oxide Nanoparticles for Highly Sensitive Interaction with Volatile Organic Compounds," Sensors 2019, 19, 918-026 (9 pages).
Rushi, A.D., et al."Exercising Substituents in porphyrins for real time selective sensing of volatile organic compounds," Sensors and Actuators B: Chemical, vol. 257, 2018, pp. 389-397 (9 pages).
Schedin, F., et al."Detection of Individual Gas Molecules Adsorbed on Graphene," Nat. Mater. 2007, 6(9), 652-655 (11 pages).
Shao, Yuyan "Graphene Based Electrochemical Sensor and Biosensors: a Review," Electroanalysis 2010, 22, No. 10, 1027-1036 (10 pages).
Shao, Yuyan, et al."Nitrogen-doped graphene and its electrochemical applications," J. Mater. Chem., 2010, 20, 7491-7496 (6 pages).
Song, Nan, et al."Applications of pillarenes, an emerging class of synthetic macrocycles," Science China Chemistry, 2014, 57(9), 1185-1198 (15 pages).
Su, Qun, et al."Understanding Sources of Electrical Disorder in Graphene Grown by Chemical Vapor Deposition for Wafer-Scale Device Applications," ACS Appl. Nano Mater., vol. 2 (2019) 3426-3433 (26 pages).
Suk, Ji Won, et al."Transfer of CVD-Grown Monolayer Graphene onto Arbitrary Substrates," ACS Nano 2011, 5(9), 6916-6924 (10 pages).
Swanson, Emily, et al."Self Assembly of Monolayers on Graphene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).
Szejtli, Jozef "Introduction and General Overview of Cyclodextrin Chemistry," Chem. Rev. 1998, 98, 1743-1753 (12 pages).
Terse-Thakoor, Trupti, et al."Graphene based biosensors for healthcare," J. Mater. Res. 2017, 32(15), 2905-2929 (25 pages).
Turkevich, John, et al."A study of the nucleation and growth processes in the synthesis of colloidal gold," Discuss. Faraday Soc., 1951,11, 55-75 (23 pages).
Vincent, Mark A., et al."Accurate Prediction of Adsorption Energies on Graphene, Using a Dispersion-Corrected Semiempirical Method Including Solvation," J. Chem. Inf. Model. 2014, 54, 2225-2260 (6 pages).
Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).
Wang, Qing Hua, et al."Room-temperature molecular-resolution characterization of self-assembled organic monolayers on epitaxial graphene," Nature Chemistry 2009 vol. 1 (3), 206-211 (6 pages).
Wei, Jinwei, et al."Understanding asymmetric transfer characteristics and hysteresis behaviors in graphene devices under different chemical atmospheres," Carbon 156 (2020) 67-76 (10 pages).
Wu, Ting, et al."Quantitative principles for precise engineering of sensitivity in carbon-based electrochemical sensors," Adv. Mater. 2018,1805752 (27 pages).
Xu, Huifeng, et al."Direct Electrochemixtry and electrocatalysis of hemoglobin protein entrapped in graphene and chitosan composite film," Talanta 81 (2010) 334-338 (5 pages).
Xu, Mengjian, et al."Gate-polarity-dependent doping effects of H2O adsorption on graphene/SiO2 field-effect transistors," J. Phys. D: Appl. Phys. 53 455301, 2020, (8 pages).
Xu, Shicai, et al."Real-time reliable determination of binding kinetics of DNA hybridization using a multi-channel graphene biosensor," Nat. Commun. 2017, 8(1) 11 pages.
Xu, Yuxi, et al."Flexible Graphene Films via te Filtration of Water-Soluble Noncovalent Functionalized Graphene Sheets," J. Am. Chem. Soc. 2008, 130, 5856-5857 (2 pages).
Yavari, Fazel, et al."Graphene-Based Chemical Sensors," J. Phys. Chem. Lett. 2012, 3, 1746-1753 (8 pages).
Yildiz, Ibrahim "A DFT Approach to the Mechanistic Study of Hydrozone Hydrolysis," J. Phys. Chem. A 2016, 120 (20), 3683-92 (25 pages).

(56) References Cited

OTHER PUBLICATIONS

Zhang, Yiheng, et al."Direct Measurements of the Interaction between Pyrene and Graphite in Aqueous Media by Single Molecule Force Spectroscopy: Understanding the π-π Interactions," Langmuir 2007, 23, 7911-7915 (5 pages).

Zhao, Yan-Li, et al."Noncovalent Functionalization of Single-Walled Carbon Nanotubes," Accounts of Chemical Research 2009, vol. 42, No. 8. 1161-1171 (12 pages).

Zheng, Peiru, et al."Oxidation of graphene with variable defects: alternately symmetrical escape and self-restructuring of carbon rings," Nanoscale 2020, 12(18), 10140-10148 (10 pages).

Zhu, Congzhi, et al."Mingling Electronic Chemical Sensors with Supramolecular Host-Guest Chemistry," Current Organic Chemistry, 2014, 18, 1957-1964 (8 pages).

Zhu, Yanwu, et al."Graphene and Graphene Oxide: Synthesis, Properties, and Applications," Adv. Mater. 2010, 22, 3906-3924 (19 pages).

"Communication Pursuant to Article 94(3) EPC," for European Patent Application No. 17794832.0 dated Mar. 16, 2023 (7 pages).

"Non-Final Office Action," for U.S. Appl. No. 16/696,348 dated Mar. 24, 2023 (22 pages).

"Response to Communication Pursuant to Article 94(3) EPC," for European Patent Application No. 20214733.6 filed May 23, 2023 (45 pages).

"Response to Final Rejection," dated Nov. 3, 2022, for U.S. Appl. No. 16/696,348, submitted via EFS-Web on Mar. 3, 2023, 11 pages.

"Second Office Action," for Chinese Patent Application No. 201810782878.3 dated Feb. 25, 2023 (4 pages) with English Summary.

Huang, Qing-An, et al. "LC Passive Wireless Sensors Toward a Wireless Sensing Platform: Status, Prospects, and Challenges," Journal of Microelectromechanical Systems, vol. 25, No. 5, Oct. 2016, https://ieeexplore.ieee.org/abstract/document/7558121 (20 pages).

* cited by examiner

SYSTEMS AND METHODS FOR ANALYTE SENSING IN PHYSIOLOGICAL GAS SAMPLES

This application is a continuation of U.S. application Ser. No. 16/037,218, filed Jul. 17, 2018, which claims the benefit of U.S. Provisional Application No. 62/533,916, filed Jul. 18, 2017, the contents of which are herein incorporated by reference in their entirety.

FIELD

Embodiments herein relate to systems and devices for analyte sensing in physiological gas samples. More specifically, embodiments herein relate to systems and devices for measuring analyte presence on graphene varactors.

BACKGROUND

In the process of providing health care, clinicians often make physical observations and run tests to gather data about a patient. After collecting data and analyzing other aspects, such as a given patient's health history, the clinician often forms a diagnosis and then selects a therapy to treat the diagnosed condition.

Knowledge of the presence and/or concentrations of various chemical analytes, such as volatile organic compounds, can be extremely useful in forming a diagnosis. However, measuring such chemical analytes in a clinically practical manner remains technically challenging.

SUMMARY

Embodiments herein relate to systems and devices for analyte sensing in physiological gas samples.

In a first aspect, a system for measuring analyte presence on a graphene varactor is included. The system can include a capacitance to digital converter (CDC) and a graphene varactor. The CDC can be in electrical communication with the graphene varactor and can be configured to measure the capacitance of the graphene varactor in response to an excitation signal over a plurality of DC bias voltages.

In a second aspect, in addition to or in place of other aspects herein, the system can further include a multiplexor configured to selectively provide electrical communication between the CDC and a plurality of graphene varactors.

In a third aspect, in addition to or in place of other aspects herein, an excitation signal can be applied to a selected graphene varactor through the multiplexor.

In a fourth aspect, in addition to or in place of other aspects herein, the excitation signal can include an alternating voltage component.

In a fifth aspect, in addition to or in place of other aspects herein, the amplitude of the excitation signal is fixed by the CDC.

In a sixth aspect, in addition to or in place of other aspects herein, a controller circuit can be included and can be configured to receive an electrical signal reflecting the capacitance of the graphene varactor.

In a seventh aspect, in addition to or in place of other aspects herein, the controller circuit can include a microcontroller.

In an eighth aspect, in addition to or in place of other aspects herein, the system further includes an electronic component in electrical communication with the controller circuit and the CDC, the electronic component selected from the group consisting of an I2C or an SPI.

In a ninth aspect, in addition to or in place of other aspects herein, the graphene varactor can include a functionalized graphene varactor.

In a tenth aspect, in addition to or in place of other aspects herein, the controller circuit is configured to calculate at least one parameter for the graphene varactor selected from the group consisting of maximum slope of capacitance to voltage; change in maximum slope of capacitance to voltage over a baseline value; minimum slope of capacitance to voltage; change in minimum slope of capacitance to voltage over a baseline value; minimum capacitance; change in minimum capacitance over a baseline value; voltage at minimum capacitance; change in voltage at minimum capacitance; maximum capacitance; change in maximum capacitance; ratio of maximum capacitance to minimum capacitance; response time constant; and ratios of any of the foregoing between the graphene varactor and a second graphene varactor.

In an eleventh aspect, in addition to or in place of other aspects herein, the graphene varactor(s) are grounded.

In a twelfth aspect, in addition to or in place of other aspects herein, the graphene varactor(s) are in electrical communication with an independent excitation output of the CDC.

In a thirteenth aspect, in addition to or in place of other aspects herein, the system can further include one or more programmable digital to analog converters (DACs) in series with the plurality of graphene sensors.

In a fourteenth aspect, in addition to or in place of other aspects herein, the system can further include a switch, the CDC in electrical communication with the switch and controlling the switch to selectively provide communication with output voltages of two programmable digital to analog converters (DACs), the programmed voltage difference between the DACs determining the excitation amplitude, and the difference between the programmed average voltage of the DACs and the bias at the CDC input determining the DC bias.

In a fifteenth aspect, a method for measuring analyte presence on a graphene varactor is included. The method can include measuring a capacitance of the graphene varactor over a range of DC bias voltages; comparing the measured capacitance at one or more DC bias voltages to one or more corresponding baseline capacitance values; and determining the presence or absence of an analyte based on the comparison.

In a sixteenth aspect, in addition to or in place of other aspects herein, the method can further include determining one or more aspects selected from the group consisting of maximum slope of capacitance to voltage; change in maximum slope of capacitance to voltage over a baseline value; minimum slope of capacitance to voltage; change in minimum slope of capacitance to voltage over a baseline value; minimum capacitance; change in minimum capacitance over a baseline value; voltage at minimum capacitance; change in voltage at minimum capacitance; maximum capacitance; change in maximum capacitance; ratio of maximum capacitance to minimum capacitance; response time constant; and ratios of any of the foregoing between two different graphene sensors.

In a seventeenth aspect, in addition to or in place of other aspects herein, the method can further include forming a capacitance to voltage curve from the measured capacitance of the graphene varactor over the range of DC bias voltages.

In an eighteenth aspect, in addition to or in place of other aspects herein, the method can further include comparing the formed capacitance to voltage curve with a baseline capacitance to voltage curve.

In a nineteenth aspect, in addition to or in place of other aspects herein, the method can further include distinguishing between different analytes binding to the graphene varactor.

In a twentieth aspect, in addition to or in place of other aspects herein, the range of DC bias voltages is from −3 V to 3 V.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Volatile organic compounds, as sensed in breath samples or other gas samples, can provide valuable information about the health status of a patient. In particular, patterns of volatile organic compounds (including the presence, absence, and/or concentration of a plurality of different volatile organic compounds) in a breath or gas sample of a patient can be associated with various disease states and/or particular health statuses. The disease states can include, but are not limited to, lung cancer, colon cancer, pulmonary disease (e.g. asthma, COPD), cardiovascular disease (e.g. heart failure), infectious diseases, digestive and inflammatory diseases (e.g. inflammatory bowel diseases such as Crohn's, colitis, or the like) or diabetes.

Graphene varactors are one type of device that can be used to measure volatile organic compounds. Various properties of graphene varactors, such as capacitance, can change in response to the presence of volatile organic compounds thereon. However, measurement of properties of the graphene varactors, such as capacitance, remains technically challenging.

However, embodiments herein can be used to rapidly and accurately measure the capacitance of a plurality of graphene varactors.

Figure 1:
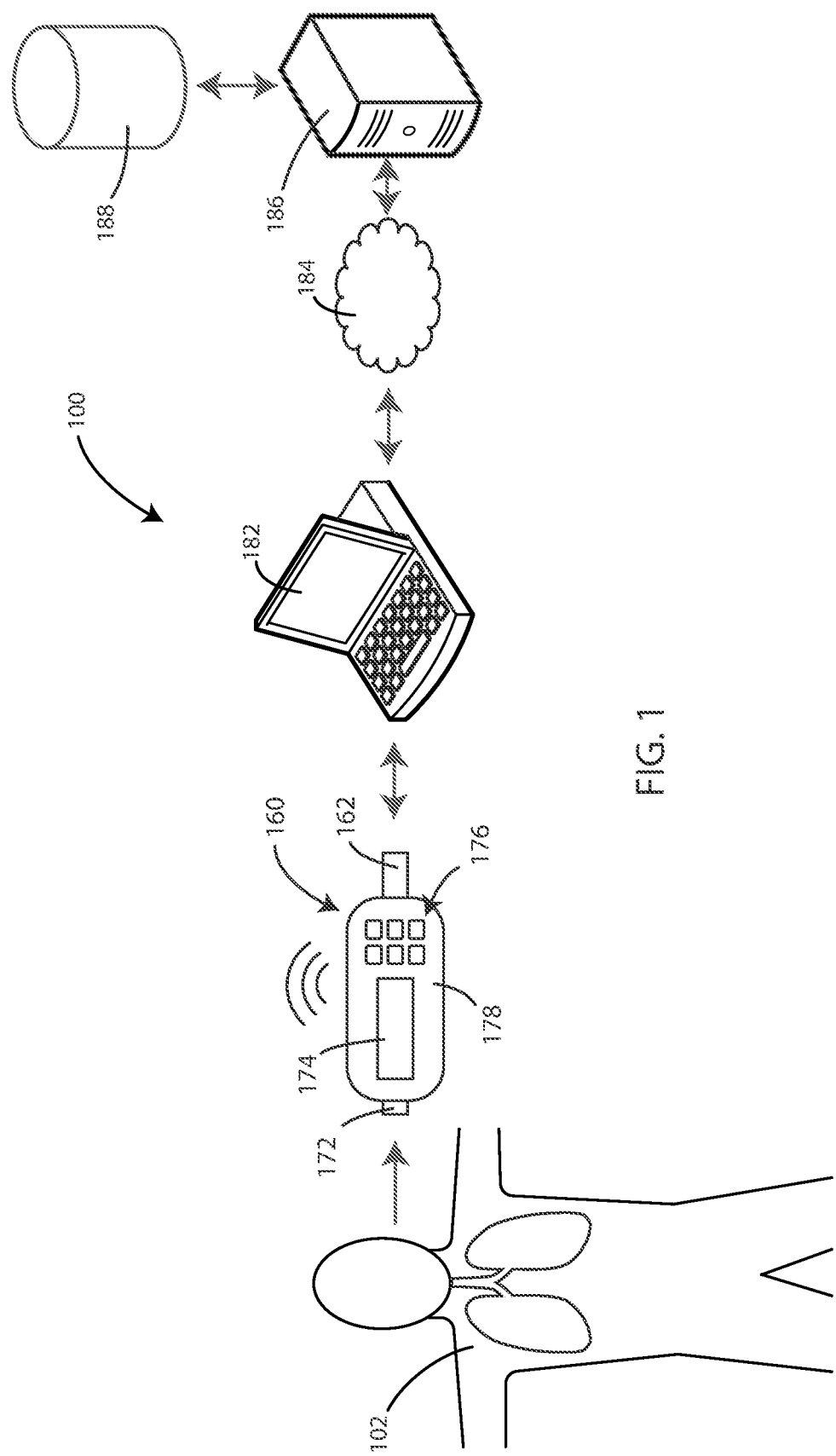
FIG. 1 is a schematic view of various components of a system in accordance with various embodiments herein.

Referring now to FIG. 1, a schematic view is shown of possible components of a system 100 in accordance with various embodiments herein. The system 100 can include a breath sensing device 160 for sensing gaseous analytes (or volatile organic compounds) in accordance with various embodiments herein. In this embodiment, the system is in a hand-held format. It will be appreciated, however, that many other formats for the system are contemplated herein.

The breath sensing device 160 can include a housing 178. The breath sensing device 160 can include a mouthpiece 162 into which a subject to be evaluated can blow a breath sample. The breath sensing device 160 can also include a display screen 174 and a user input device 176, such as a keyboard. The breath sensing device 160 can also include a gas outflow port 172. Aspects of breath sensing systems and devices are described in U.S. Publ. Appl. No. 2016/0109440, the content of which is herein incorporated by reference. While FIG. 1 shows a breath sensing device, it will be appreciated that other types of gas sampling systems can also be used herein. For example, gas sampling devices for use with catheters and endoscopy systems can also be used. An exemplary gas sampling device in the context of a catheter or endoscopy device is described in U.S. Appl. No. 62/350,345, the content of which is herein incorporated by reference.

In some embodiments, the system 100 can include a local computing device 182 that can include a microprocessor, input and output circuits, input devices, a visual display, a user interface, and the like. In some embodiments, the breath sensing device 160 can communicate with the local computing device 182 in order to exchange data between the breath sensing device 160 and the local computing device 182. The local computing device 182 can be configured to perform various processing steps with the data received from the breath sensing device 160, including, but not limited to, calculating various parameters described herein. However, it should be appreciated that in some embodiments the features associated with the local computing device 182 can be integrated into the breath sensing device 160. In some embodiments, the local computing device 182 can be a laptop computer, a desktop computer, a server (real or virtual), a purpose dedicated computer device, or a portable computing device (including, but not limited to, a mobile phone, tablet, wearable device, etc.).

The local computing device 182 and/or the breath sensing device 160 can communicate with computing devices in remote locations through a data network 184, such as the Internet or another network for the exchange of data as packets, frames, or otherwise.

In some embodiments, the system 100 can also include a computing device such as a server 186 (real or virtual). In some embodiments, the server 186 can be located remotely from the breath sensing device 160. The server 186 can be in data communication with a database 188.

The database 188 can be used to store various patient information, such as that described herein. In some embodiments, the database can specifically include an electronic medical database containing data regarding the health status of a patient, patterns of data associated with various conditions (such as that generated from machine learning analysis of large sets of patient data), demographic data and the like.

Figure 2:
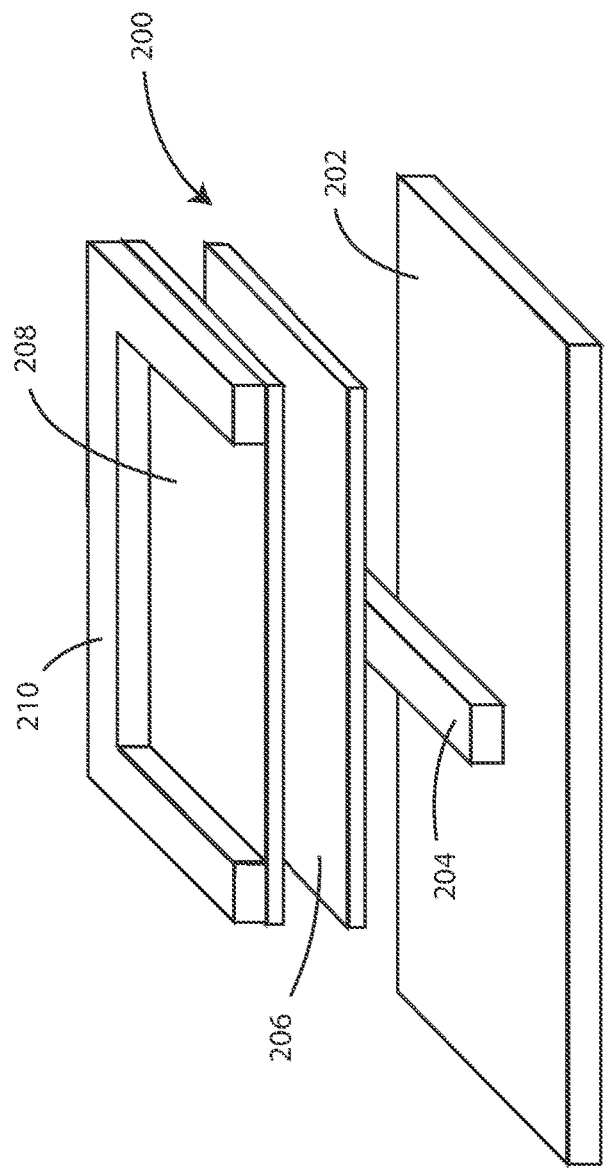
FIG. 2 is a schematic exploded view of a graphene varactor in accordance with various embodiments herein.

Graphene varactors can be prepared in various ways and with various geometries. Referring now to FIG. 2, an exploded view of a graphene varactor 200 is shown. The graphene varactor 200 can include an insulator layer 202, a gate electrode 204, a dielectric layer 206, a graphene layer 208, and a contact electrode 210.

Figure 3:
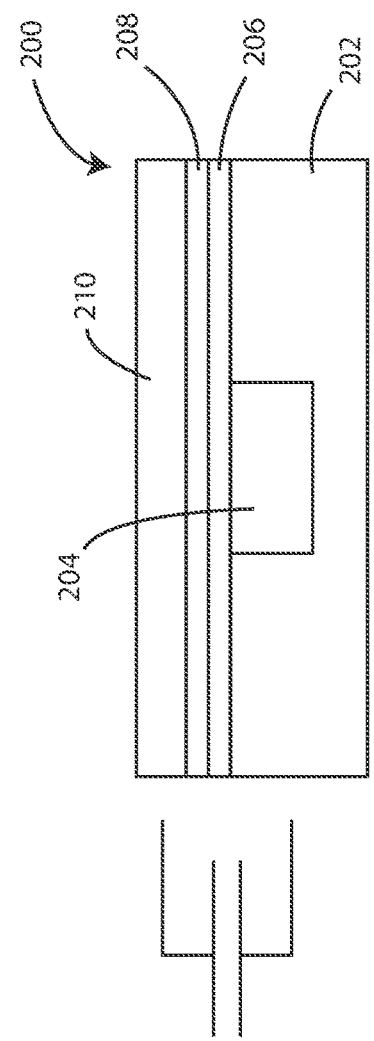
FIG. 3 is a schematic cross-sectional view of a graphene varactor in accordance with various embodiments herein.

FIG. 3 shows a cross-sectional view of the graphene varactor 200. As is shown, the gate electrode 204 can be recessed into the insulator layer 202. The gate electrode 204 can be formed by etching a depression into the insulator layer 202 and then depositing an electrically conductive material in the depression to form the gate electrode 204. The insulator layer 202 can include various materials. In some embodiments the insulator layer 202 can be silicon dioxide formed on a silicon substrate (wafer). The dielectric layer 206 can be formed on a surface of the insulator layer 202 and the gate electrode 204. In some examples, the dielectric layer 206 can be formed of a material, such as, silicon dioxide, aluminum oxide, hafnium dioxide, zirconium dioxide, hafnium silicate or zirconium silicate. The graphene layer 208 can be disposed on the dielectric layer 206. In some aspects, the graphene layer 208 can be a graphene monolayer. A contact electrode 210 can also be disposed on the surface (or a portion thereof) of the graphene layer 208. Aspects of exemplary graphene varactors can be found in U.S. Publ. App. No. 2014/0145735, the content of which is herein incorporated by reference. Further aspects of gas and/or breath sampling systems are described in U.S. Publ. Appl. No. 2016/0109440, the content of which is herein incorporated by reference.

In various embodiments, the graphene layer can be functionalized to make the graphene sensor specific for a particular analyte or class of analytes. As analytes bind to the graphene layer, the capacitance of the sensor changes. Further, as shown below with regard to FIGS. 8-9, the capacitance changes differently based on the voltage of the excitation current.

Figure 4:
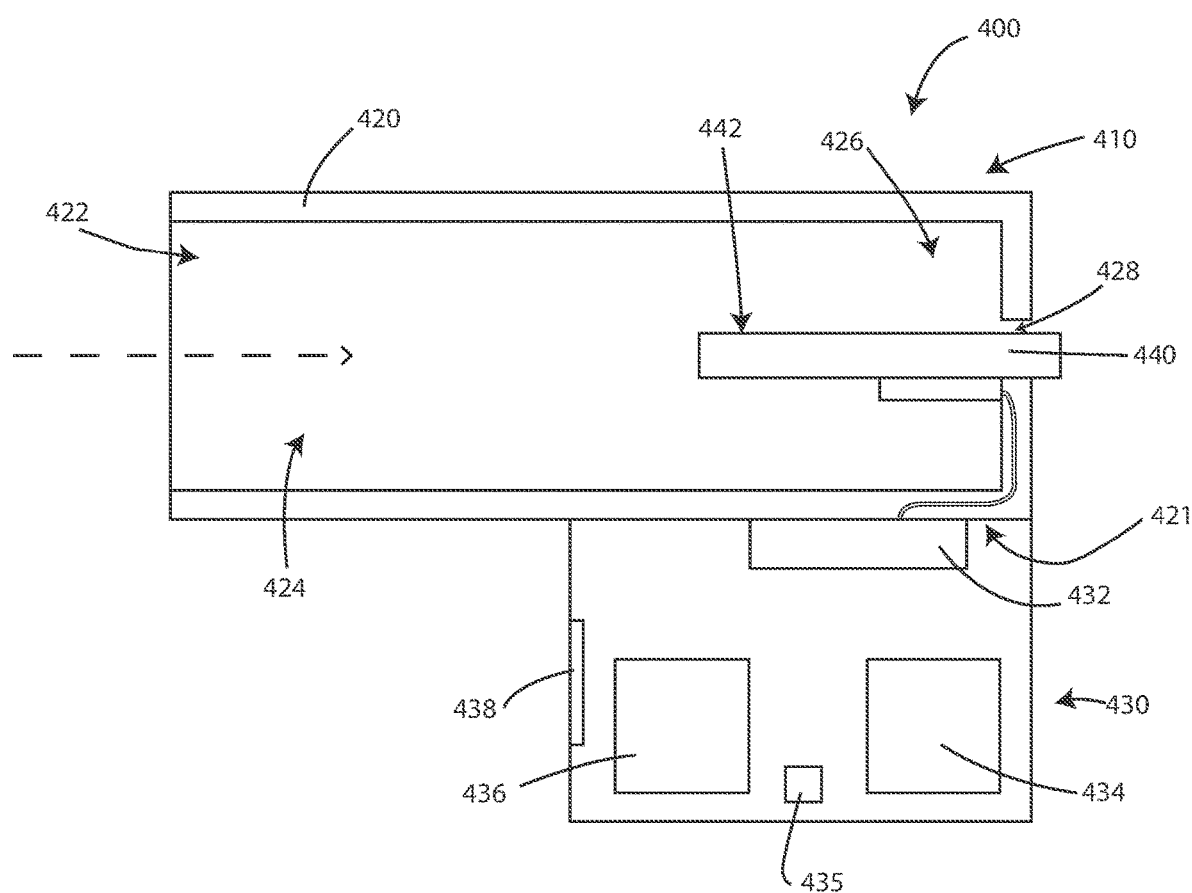
FIG. 4 is a schematic cross-sectional view of elements of a gas sensing device consistent with the technology disclosed herein.

Systems herein can also include a breath and/or gas sensing device or system. In particular, systems herein can gather data on the presence, absence, and/or amount of various gaseous analytes including, but not limited to, volatile organic compounds. FIG. 4 is a schematic cross-sectional view of an example system 400 consistent with the technology disclosed herein. It will be appreciated that this schematic view has been simplified for ease of illustration and that embodiments of systems and devices herein can include various features not shown in FIG. 4. In addition, some embodiments of systems and devices herein may lack various features shown in FIG. 4. The system 400 is generally configured for collecting a gas sample and communicating data associated with the gas sample. The system 400 has a gas sampling device 410 and a docking station 430.

The gas sampling device 410 can be configured to collect a gas sample and facilitate testing of the gas sample to generate data. In some embodiments, the gas sampling device 410 can be configured as a handheld device. In such cases, the gas sampling device can be configured to be held in the hand of a care provider, a patient, or both, during certain steps of its use, while also being configured to be held or otherwise positioned in association with the docking station 430 during certain steps of its use.

In some embodiments, the gas sampling device 410 is configured to receive a gas sample, such as exhaled breath, from a patient and direct the gas sample to a testing location. The gas sampling device 410 generally has a housing 420 defining an airflow aperture 422, a gas testing chamber 426, a sensor receptacle 428, an airflow pathway 424, and a docking structure 421.

When receiving a gas sample, the gas (such as breath from a patient), can pass into the gas sampling device 410 through the airflow aperture 422, through the airflow pathway 424, into the gas testing chamber 426 and into contact with one or more measurement zones 442 of a disposable sensor test strip 440, and then out the end of the gas testing chamber 426 through the sensor receptacle 428, or through a separate exhaust port (not shown in this view). While this view depicts contact in some areas between the sensor receptacle 428 and the disposable sensor test strip 440, it will be appreciated that there can be segments or areas where the sensor receptacle 428 and the disposable sensor test strip 440 do not contact or do not create sealing contact, thus allowing for a path for the gas to flow out through the sensor receptacle 428.

While FIG. 4 shows the airflow pathway 424 to be approximately the same size as the interior space of the housing 420, it will be appreciated that this is simply for ease of illustration and that the size of the airflow pathway 424 can be, in many cases, much smaller than the entire interior size of the housing 420, allowing for room for other components within the interior of the housing 420, such as other components described herein including, but not limited to, sensors, a power source, processing devices, communication hardware, conditioning elements, and the like.

The housing 420 can be constructed of a variety of materials and combinations of materials. The housing 420 can be a single cohesive structure or can be constructed of multiple components that are coupled to form the housing 420. As an illustrative example, a portion of the housing 420 that defines the airflow pathway 424 can be coupled to the portion of the housing 420 that defines the airflow aperture 422. The portion of the housing 420 that defines the airflow pathway 424 can include a conduit or tube with various different cross-sectional sizes and shapes. The conduit or tube can be formed from various materials including, but not limited to, polymers, metals, ceramics, glass, composites or the like. In some embodiments, surfaces lining the airflow pathway 424 can be coated with materials to provide various desirable functional properties.

The airflow aperture 422 is generally configured to provide an input for the gas sample at the housing 420. In some embodiments the airflow aperture 422 is configured to be in fluid communication with a patient's mouth, although in some other embodiments a protective liner can be used to provide a barrier between the patient's mouth and the housing, which will be described in more detail, below.

The airflow pathway 424 generally is configured to direct the gas input at the airflow aperture 422 to the gas testing chamber 426. As such, the airflow pathway 424 generally extends from the airflow aperture 422 to the gas testing chamber 426. The airflow pathway 424 can have a cross-sectional area that is substantially the same along the length of the airflow pathway or it can vary. In some embodiments, the gas testing chamber 426 can have different interior dimensions (e.g., height, width, etc.) than the airflow pathway leading to it.

The gas testing chamber 426 defines a testing location for the gas sample. In various embodiments, the gas testing chamber 426 is configured to receive a measurement zone 442 of a disposable sensor test strip 440. Accordingly, the sensor receptacle 428 defined by the housing 420 is generally configured to removably retain the disposable sensor test strip 440 within the gas testing chamber 426. In various embodiments the sensor receptacle 428 is configured to slidably receive the disposable sensor test strip 440 that is manually inserted by a user. In some embodiments, the disposable sensor test strip 440 can be inserted with its long (or major) axis parallel to the long (or major) axis of the housing 420. However, in other embodiments, the disposable sensor test strip 440 can be inserted with its long (or major) axis positioned differently with respect to the long (or major) axis of the housing 420, such as perpendicular. Example sensor test strips will be described in more detail, below.

While FIG. 4 depicts the test strip located approximately in the middle of the gas sampling device 410 (top to bottom with regard to the perspective of the figure), it will be appreciated that the test strip can be positioned biased toward the top or the bottom, to be closer to an exterior surface of the housing 420 or gas sampling device 410. In some embodiments, the disposable sensor strip can be positioned less than 5 cm, 4 cm, 3 cm, 2 cm, 1 cm, 0.5 cm, 0.2 cm or less from exterior surface (or exterior wall) of the housing 420.

The docking station 430 is generally configured to collect data generated from testing the gas sample. The docking station 430 has a reading device 432 that can include circuitry to measure the capacitance of a plurality of graphene sensors. Aspects of circuitry to measure the capacitance of the graphene sensors is described in greater detail below. However, it will be appreciated that in some embodiments, such circuitry can all be disposed in the gas sampling device 410, can all be disposed in the docking station 430, or can be distributed with some components in the gas sampling device 410 and some components in the docking station 430. Indeed, in some cases there may not be a separate docking station and functionality attributed thereto herein can simply be integrated into the gas sampling device.

In various embodiments, the reading device 432 can also be configured to both baseline data and sample data from the disposable sensor test strip 440—where the term "baseline data" is defined as data collected before exposure of the disposable sensor test strip 440 to the gas sample or the patient or test subject and wherein the term "sample data" refers to data specific to the gas sample of the patient or test subject. In some cases the baseline data can reflect conditions of whatever gas happens to be in the testing chamber prior to obtaining a gas sample of a patient. However, in other embodiments, ambient air can purposefully be pushed through the testing chamber, and/or a particular reference gas sample of known composition can be put into the testing chamber for purposes of generating baseline data.

The docking station 430 is generally configured to be a docking location for the gas sampling device 410. The docking station 430 is generally configured to physically receive the gas sampling device 410. The docking station 430 can receive the gas sampling device 410 through a variety of structures and configurations that will be appreciated by those having ordinary skill in the art. In various embodiments the docking station 430 and the docking structure 421 of the gas sampling device 410 have a mating configuration by which the docking station 430 receives the docking structure 421 of the gas sampling device 410. In some such embodiments the docking station 430 and the docking structure 421 define an interference fit. However, in other embodiments, the docking station 430 can simply rest upon or in the docking structure 421. In some embodiments the docking station 430 and the docking structure 421 are configured to position the disposable sensor test strip 440 and the reading device 432 in sufficient proximity to accommodate transmission of data between the reading device 432 and disposable sensor test strip 440. In some embodiments the docking station and the docking structure are configured to position the disposable sensor test strip 440 and the reading device 432 within 6 cm, 5 cm, 4 cm, 3 cm, or 2 cm of each other, or even within 1 cm of each other.

The docking station 430 can have various additional components. In some embodiments the docking station 430 has a processor 436 and memory 435. The processor 436 and memory 435 can be configured to process and store data obtained from the tested gas sample. For example, the memory 435 can store baseline data locally and the processor 436 can be configured to remove collected baseline data from the tested gas data to obtain adjusted data. Such adjusted data can remove some impact of the ambient environment on the tested gas data. In another example, the processor can be configured to compare the adjusted data (or, in some embodiments the tested gas data) to known data indicative of one or more diseases. Such a comparison can be used to identify the presence of a particular disease using a comparative algorithm. In yet another example, the processor of the docking station 430 can be configured to identify a defect in the disposable sensor test strip 440. Example defects can include manufacturing defects and/or premature exposure to ambient gases. The docking station 430 can be configured to collect, save, and potentially transmit records of such defects.

The docking station 430 has networking hardware 434 in various embodiments. The networking hardware 434 can be configured to transmit data over a network to a remote system, including a cloud-based system. In some implementations the remote system can be a hospital, clinic, laboratory, or other location. In some embodiments the networking hardware 434 is configured to transmit data generated from testing the gas sample. The networking hardware 434 is configured to transmit baseline data in some embodiments. The networking hardware is configured to transmit adjusted data in some embodiments. In some embodiments the remote system analyzes the data it receives. For example, in some embodiments the remote system is configured to compare the adjusted data to known data indicative of a plurality of diseases. That comparison can identify the presence of a particular disease.

In some embodiments the docking station 430 has a user interface 438. The user interface 438 can be configured to communicate information to a user. For example, the user interface 438 can be configured to communicate an active data transmission, such as a data transmission between the docking station 430 and the gas sampling device 410 and/or between the docking station 430 and a network. In some embodiments the user interface 438 can be configured to communicate information about the current stage of the testing process, progress of the same, or what steps are next or what actions are required. For example, in some cases the user interface 438 can be configured to communicate that that the gas sampling device 410 is ready to receive a gas sample or that the docking station 430 has finished reading data from the gas sampling device 410. The user interface 438 can also be configured to communicate a defect in the sensor test strip. The user interface 438 can be configured to communicate through visual notification, audio notification, and the like. As a specific example, a flashing light can be used to indicate that the docking station 430 is transmitting data. The user interface 438 can include a light source such as an LED or similar light emitting device.

One example approach to using the system depicted in FIG. 4 will now be described. A disposable sensor test strip 440 is inserted into the gas sampling device 410 such that it is received by the gas testing chamber 426 defined by a housing of a gas sampling device. The gas sampling device 410 having the disposable sensor test strip 440 is docked to the docking station 430, and the reading device 432 of the docking station 430 reads baseline data from the disposable sensor test strip 440 through the housing 420 of the gas sampling device 410. The gas sampling device 410 is undocked from the docking station 430 after reading the baseline data, and a gas sample is received by the gas testing chamber such that the gas sample is brought into contact with the disposable sensor test strip 440. For example, the gas sampling device 410 may be physically grasped by a care provider and removed from the docking station 430 and physically handed to a patient or test subject who may then blow into the gas sampling device 410 to provide the gas sample to be analyzed. In other cases, the gas sampling device 410 may be held by the care provider instead of being held by the patient or test subject. The gas sampling device 410 can then be docked to the docking station 430 after receiving the gas sample, and the data from the tested gas is read from the disposable sensor test strip 440 by the reading device 432, wherein the adjusted data is read through the housing 420 of the gas sampling device 410. In various embodiments the disposable sensor test strip 440 is configured to be single-use. As such, the disposable sensor test strip 440 can be disposed of following the collection of sample gas data from the disposable sensor test strip 440. Various other methods of using the system depicted in FIG. 4 are also contemplated.

The measurement zones 442 can include a plurality of discrete binding detectors that can include one or more analyte binding receptors bound thereto. In some embodiments, all of the analyte binding receptors within a particular discrete binding detector can be the same with respect to their analyte binding properties. In other embodiments, at least some of the analyte binding receptors within a particular zone can be different from one another with respect to their analyte binding properties. In some embodiments, each discrete binding detector can be unique. In some embodiments, discrete binding detectors that are unique can be cross-reactive in that they bind to different portions or different configurations of the same chemical compound.

The plurality of graphene varactors can include those that are specific for different volatile organic compounds. In some embodiments, the plurality of graphene varactors can detect the presence of at least 5, 10, 15, 20, 30, 40 or more different volatile organic compounds. In some embodiments, the number of different volatile organic compounds detected by the graphene varactors can be in a range wherein any of the forgoing numbers can serve as the upper or lower bound of the range provided that the upper bound is greater than the lower bound.

As referenced above, the capacitance of the graphene sensor can be measured by delivering an excitation current at a particular voltage and/or over a range of voltages. Measuring the capacitance provides data that reflects the binding status of analytes to the graphene sensor. Various measurement circuitry can be used to measure the capacitance of the graphene sensor.

Figure 5:
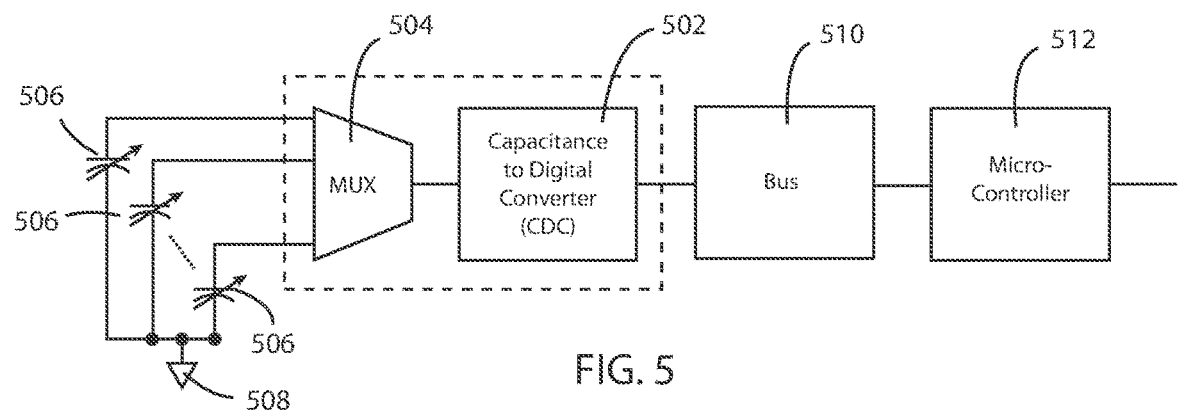
FIG. 5 is a schematic diagram of circuitry to measure the capacitance of a plurality of graphene sensors in accordance with various embodiments herein.

Referring now to FIG. 5, a schematic diagram is shown of circuitry to measure the capacitance of a plurality of graphene sensors. The circuitry can include a capacitance to digital converter (CDC) 502 in electrical communication with a multiplexor 504. The multiplexor 504 can provide selective electrical communication with a plurality of graphene varactors 506. The other side of the graphene varactors 506 can be in electrical communication with a ground 508.

In some embodiments, the CDC 502 can be in electrical communication with a bus device 510. The bus device 510 can include various specific components, but in some embodiments can be selected from the group consisting of an I$^2$C or an SPI. The bus device 510 can, in turn, be in electrical communication with a controller or processor. For example, the bus device 510 can be in electrical communication with a microcontroller 512. The microcontroller 512 can, in turn, be in communication with other components of the device or system. In will be appreciated that not all of the components illustrated in FIG. 5 may be separate from one another. On the contrary, various components can be integrated together, including, but not limited to, the multiplexor 504, the CDC 502, and the bus device 510.

In operation, the excitation signal (an alternating voltage) is applied to the selected capacitor through the multiplexor and the electronic charge required to charge and discharge the graphene varactor is measured to determine the capacitance. The amplitude of the excitation signal is fixed by the CDC 502. The bias voltage at which the capacitance is measured is equal to the average voltage of the excitation signal. An exemplary CDC for this type of configuration includes Texas Instruments model FDC1004. The FDC1004 has an integrated multiplexor and I$^2$C. It will be appreciated that many other types of CDCs can also be used.

In some embodiments, the graphene varactors may not be grounded. The other side of the graphene varactors can be connected to another device. For example, in some embodiments the other side of the graphene varactors can be connected to an independent excitation output of the CDC or another component. In this case, an excitation signal (again, an alternating voltage) is applied to all of the capacitors in the sensor array, and electronic charge required to charge and discharge the selected graphene varactor is measured through the multiplexor to determine the capacitance. The amplitude of the excitation signal is set by the CDC. The bias voltage at which the capacitance is measured is equal to the difference between the bias voltage at the CDC input (via the multiplexor, usually equal to VCC/2, where VCC is the supply voltage) and the average voltage of the excitation signal. Since the excitation voltage is typically centered about VCC/2 for this type of CDC, the bias voltage is typically fixed at zero volts.

Figure 6:
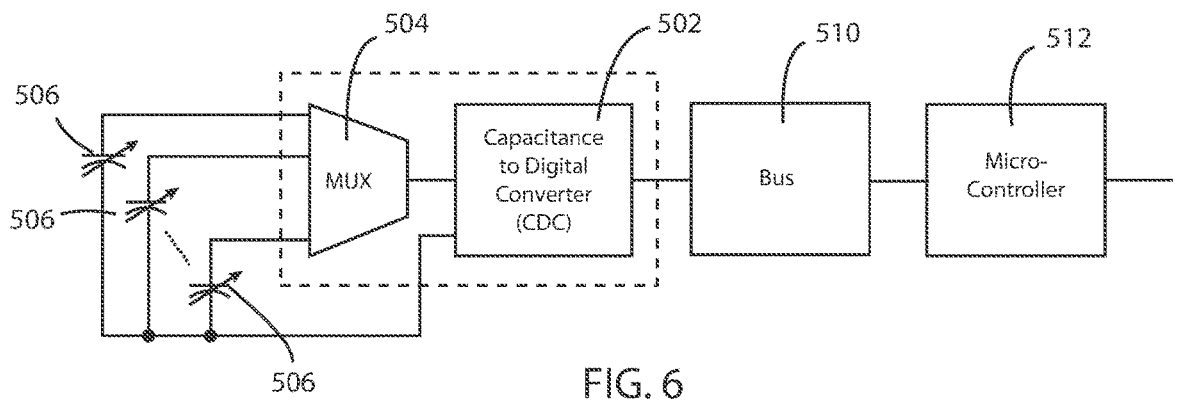
FIG. 6 is a schematic diagram of circuitry to measure the capacitance of a plurality of graphene sensors in accordance with various other embodiments herein.

Referring now to FIG. 6, a schematic diagram is shown of circuitry to measure the capacitance of a plurality of graphene sensors in accordance with another embodiment herein. The circuitry can include a capacitance to digital converter (CDC) 502 in electrical communication with a multiplexor 504. The multiplexor 504 can provide selective electrical communication with a plurality of graphene varactors 506. In this embodiment, the other side of the graphene varactors 506 can be in electrical communication with an independent excitation output of the CDC.

The change in capacitance of the graphene varactor based on analyte binding depends on the excitation voltage used to measure the capacitance. Because of this, a greater amount of information can be gathered by varying the voltage of the excitation signal across a range of voltages. Various techniques can be used to achieve this. However, in some embodiments, a pair of programmable digital to analog converters with different output voltages can be used in combination with a switch in order to achieve variation in the voltage of the excitation signal.

Figure 7:
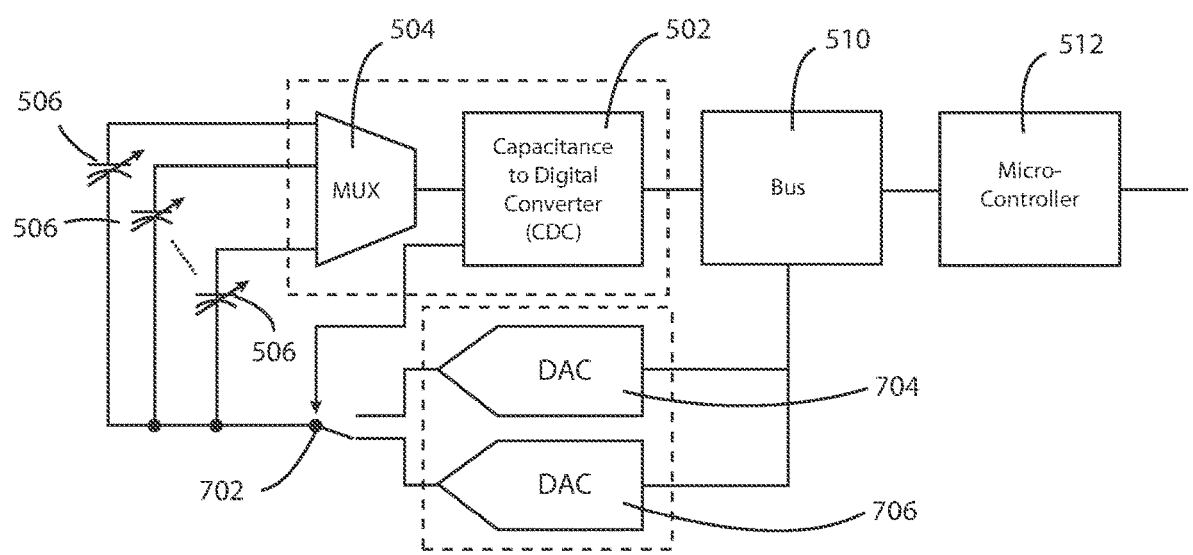
FIG. 7 is a schematic diagram of circuitry to measure the capacitance of a plurality of graphene sensors in accordance with various other embodiments herein.

Referring now to FIG. 7, a schematic diagram is shown of circuitry to measure the capacitance of a plurality of graphene sensors in accordance with another embodiment herein. The circuitry can include a capacitance to digital converter (CDC) 502 in electrical communication with a multiplexor 504. The multiplexor 504 can provide selective electrical communication with a plurality of graphene varactors 506. The connection to the other side of the graphene varactors 506 can be controlled by a switch 702 (as controlled by the CDC) and can provide selective electrical communication with a first digital to analog converter (DAC) 704 and a second digital to analog converter (DAC) 706. The other side of the DACs 704, 706 can be connected to a bus device 510, or in some cases, the CDC 502.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V.

Many different aspects can be calculated based on the capacitance data. For example, aspects that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different graphene sensors and particularly between different graphene sensors having specificity for different analytes.

The above calculated aspects can be used for various diagnostic purposes. In some cases, the above calculated aspects can be indicative of the identity and/or concentrations of specific volatile organic components of a gas sample. As such, each of the calculated values above can serve as a distinct piece of data that forms part of a pattern for a given patient and/or given gas sample. As also described elsewhere herein, the pattern can then be matched against preexisting patterns, or patterns identified in real-time, derived from large, stored data sets through techniques such as machine learning or other techniques, wherein such patterns are determined to be characteristic of various conditions or disease states. The above calculated aspects can also be put to other purposes, diagnostic and otherwise.

In some cases calculations, such as those described above, can be performed by a controller circuit. The controller circuit can be configured to receive an electrical signal reflecting the capacitance of the graphene varactors. In some embodiments, the controller circuit can include a microcontroller to perform these calculations. In some cases the controller circuit can include a microprocessor in electrical communication with the measurement circuit. The microprocessor system can include components such as an address bus, a data bus, a control bus, a clock, a CPU, a processing device, an address decoder, RAM, ROM and the like. In some cases the controller circuit can include a calculation circuit (such as an application specific integrated circuit—ASIC) in electrical communication with the measurement circuit.

In addition, in some cases the system can include a nonvolatile memory where sensitivity calibration information for the particular sensor is stored. By way of example, the sensor could be tested in a production facility, where its sensitivity to various analytes such as VOC's can be determined and then stored on an EPROM or similar component. In addition or alternatively, sensitivity calibration information can be stored in a central database and referenced with a sensor serial number when patient data is sent to a central location for analysis and diagnosis. These components can be included with any of the pieces of hardware described herein.

In some embodiments herein, components can be configured to communicate over a network, such as the internet or a similar network. In various embodiments, a central storage and data processing facility can be included. In some embodiments, data gathered from sensors in the presence of the patient (local) can be sent to the central processing facility (remote) via the internet or a similar network, and the pattern from the particular patient being evaluated can be compared to those of thousands or millions of other patients, many of whom have been previously diagnosed with various conditions and wherein such condition data has been stored. Pattern matching algorithms can be used to find other patients or classes of patients (for example disease or condition specific classes) to which the current patient's pattern is most similar. Each class of patients can include a predetermined likelihood of having a given condition or disease state. In this manner, after pattern matching a likelihood of having a given condition or disease state can be provided back across the data network to the facility where the patient is currently at.

Methods

Embodiments herein can include various methods. Exemplary methods can include any of the approaches and/or operations described herein. In an embodiment, a method of measuring analyte presence on a graphene varactor is included. The method can include measuring a capacitance of the graphene varactor over a range of DC bias voltages, comparing the measured capacitance at one or more DC bias voltages to one or more corresponding baseline capacitance values and determining the presence or absence of an analyte based on the comparison.

In some embodiments, the method can further include determining one or more aspects including, but not limited to, maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value and voltage at minimum capacitance (Dirac point), change in voltage at minimum capacitance, maximum capacitance, change in maximum capacitance, ratio of maximum capacitance to minimum capacitance, response time constants, and ratios of any of the foregoing between different graphene sensors and particularly between different graphene sensors having specificity for different analytes.

In some embodiments, the method can include forming a capacitance to voltage curve from the measured capacitance of the graphene varactor over the range of DC bias voltages. In some embodiments, the method can include comparing the formed capacitance to voltage curve with a baseline capacitance to voltage curve. In some embodiments, the method can include distinguishing between different analytes binding to the graphene varactor. In some embodiments the method can further include measuring a capacitance of the graphene varactor over a range of DC bias voltages. In some embodiments, the range of DC bias voltages can be from −3 V to 3 V.

In some embodiments, the patient can be prompted to take a breath or gas test (where the test could be performed either in a non-clinical setting such as their home or where such a prompt could cause them to come to a clinical setting to take the test).

In some embodiments, a pattern including such things as sleep patterns (e.g. wearable, implant or non-contact in-home sensor), physiological data (autonomic tone measures), body weight (such as weight automatically measured by a mat in the house), activity levels (e.g. mobile device, wearable, implant or non-contact in-home sensor), etc. can be assessed, such as using an algorithm, and if the results of those factors so indicate, then the system can inform the user that they should administer or get a breath or gas test to detect early signs of heart failure decompensation. If a positive result, or data trends are beyond a normal range for the individual patient, then the system can inform the patient to seek medical care for early intervention.

In some embodiments, a pattern including things such as sleep patterns, autonomic tone, respiratory rate, respiratory sounds, activity levels, etc., can be used to recommend to the user that they should administer a breath test (or come to a clinic to get a breath test) to detect early signs of a COPD exacerbation or repeat exacerbation. If a positive result, or data trends beyond normal range for the individual patient, seek medical care and/or use prescribed pharmaceutical (e.g. bronchodilators, corticosteroids, etc.) for early intervention.

Beyond, heart failure decompensation and COPD, such patterns and prompts to the patient to get a breath test can also be used for diabetes management and inflammatory bowel diseases (also including data regarding dietary intake, autonomic tone, etc. in the pattern) to detect early signs of a flare-up.

EXAMPLES

Example 1: Capacitance for a Graphene Varactor Over a Range of Voltages

A graphene varactor was manufactured consistent with that described in U.S. Publ. Appl. No. 2014/0145735.

A baseline capacitance to voltage curve was established by measuring capacitance over a range of excitation voltages while flushing the sensor with nitrogen gas using an LCR meter. The DC bias voltage ranged from −0.5 volts to 0.5 volts. Using the same LCR meter, capacitance values over the same bias voltage range were also measured while flushing the sensor with a combination of nitrogen gas and octanol vapor. The total flow rate was 0.5 liters per minute in each experiment, octanol concentration was approximately 3.6 parts per million in nitrogen, sensors were exposed to the nitrogen gas and octanol vapor mixture for approximately 5 minutes before measurement for equilibration, the AC excitation signal had amplitude 50 mV and frequency 500 kHz.

Figure 8:
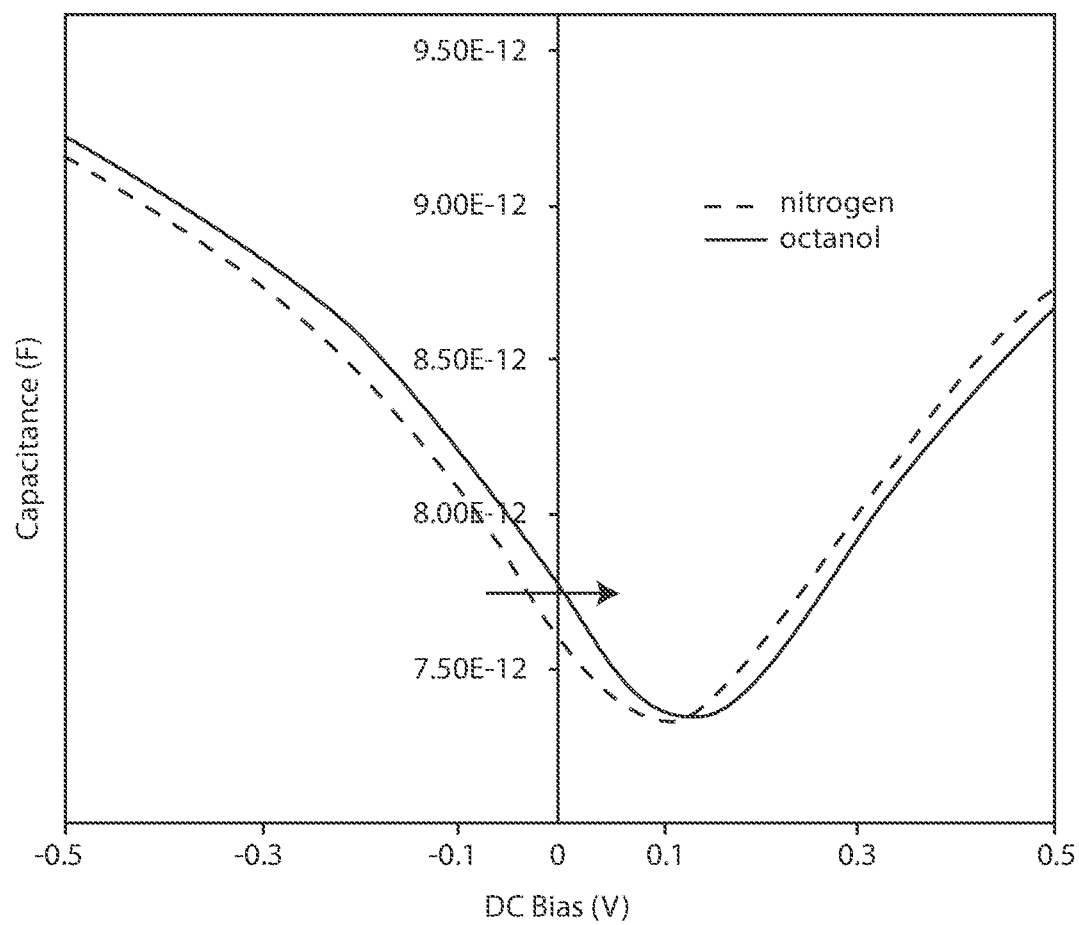
FIG. 8 is a graph showing capacitance versus DC bias voltage for a graphene varactor in accordance with various embodiments herein.

As shown in FIG. 8, it can be seen that binding of octanol caused the capacitance to voltage curve to retain the same overall shape but be shifted to the right (e.g., the minimum capacitance occurred at a higher DC bias voltage).

Example 2: Capacitance for a Graphene Varactor Over a Range of Voltages

A graphene varactor was prepared as described in Example 1. A baseline capacitance to voltage curve was established by measuring capacitance over a range of excitation voltages using an LCR meter as described above in Example 1. The DC bias voltage ranged from −1 volt to 1 volt. Using the same LCR meter, capacitance values over the same bias voltage range were also measured while flushing the sensor with a combination of nitrogen gas and acetone vapor. Details were the same as descried above in Example 1, except that the acetone concentration was approximately 25,000 parts per million.

Figure 9:
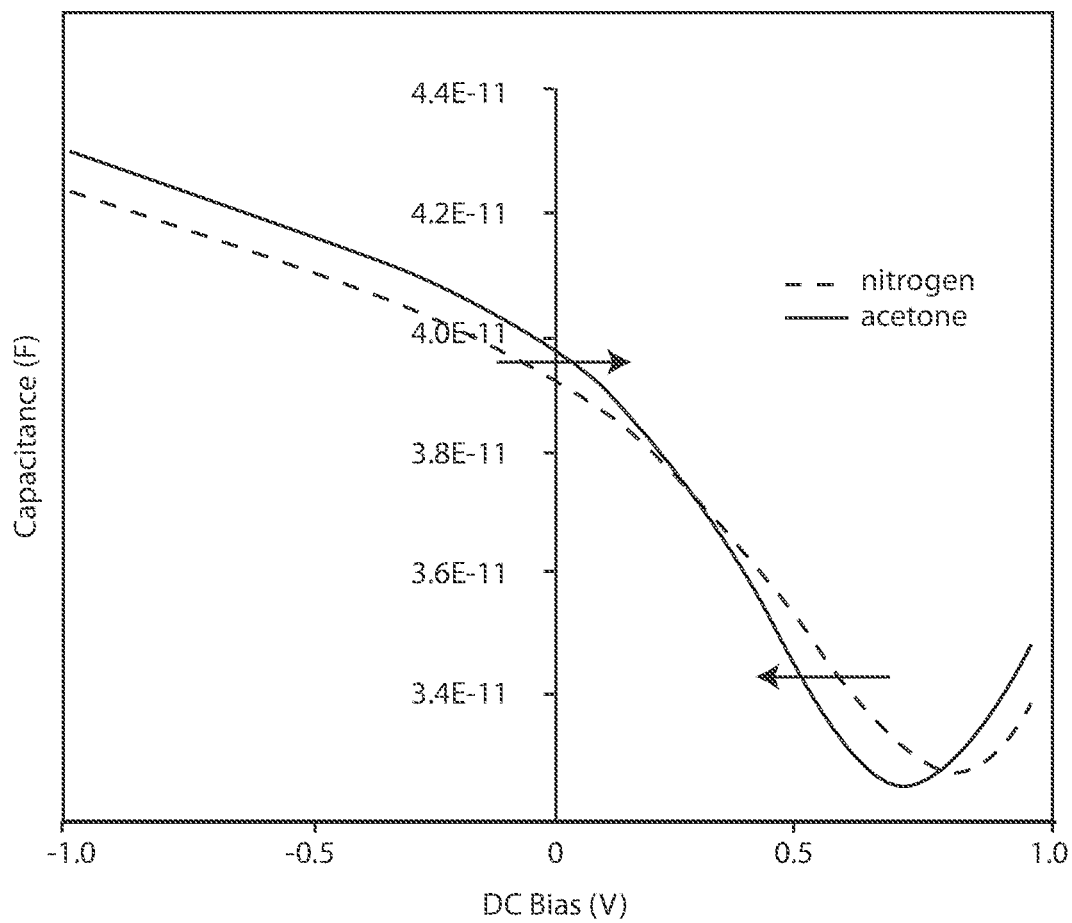
FIG. 9 is a graph showing capacitance versus DC bias voltage for a graphene varactor in accordance with various embodiments herein.

As shown in FIG. 9, it can be seen that binding of acetone caused the capacitance to voltage curve to change shape in that the top portion of the curve was shifted to the right, but the bottom portion of the curve was shifted to the left.

Example 3: Capacitance for a Functionalized Graphene Varactor Over a Range of Voltages A graphene varactor was prepared as described in Example 1. The graphene was then functionalized with pyrene-acetic acid by soaking the varactor in a 1 mM solution of pyrene acetic-acid in ethanol for 14 hours.

A baseline capacitance to voltage curve was established by measuring capacitance over a range of excitation voltages using an LCR meter as described above in Example 1. The DC bias voltage ranged from −1 volt to 1 volt. Using the same LCR meter, capacitance values over the same bias voltage range were also measured while flushing the sensor with: 1.) a combination of nitrogen gas and gaseous acetone, 1.) a combination of nitrogen gas and gaseous octane, and 3.) a combination of nitrogen gas and gaseous octanol.

Figure 10:
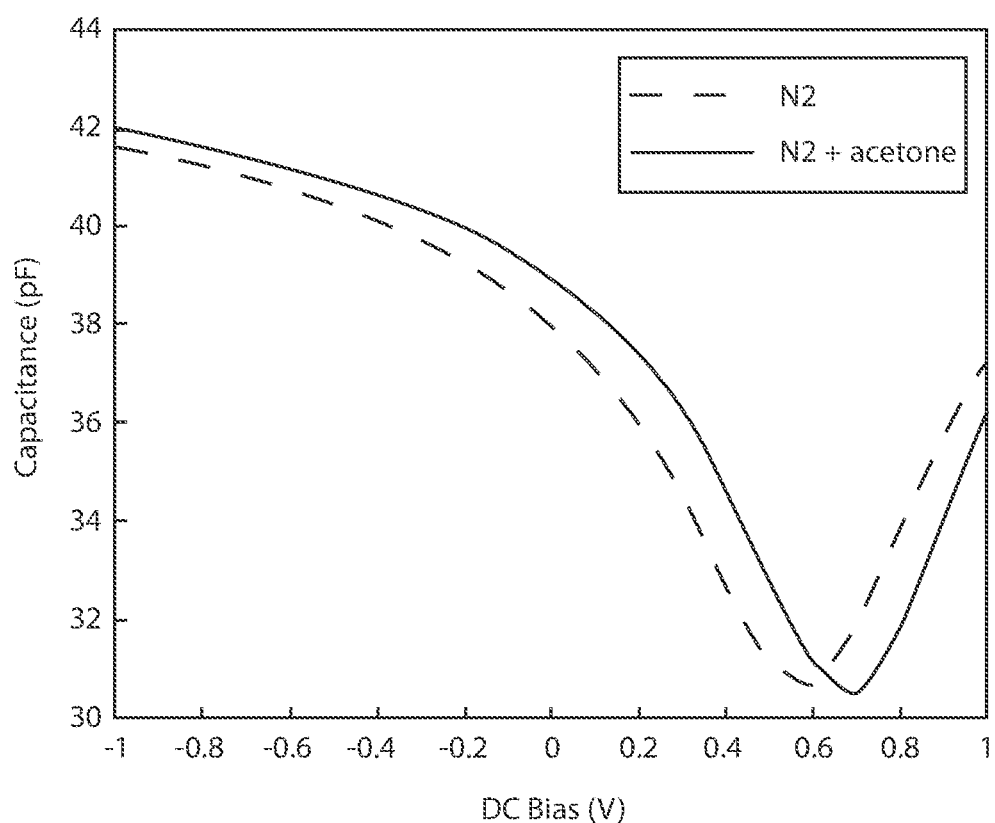
FIG. 10 is a graph showing capacitance versus DC bias voltage for a functionalized graphene varactor in response to acetone binding in accordance with various embodiments herein.
Figure 11:
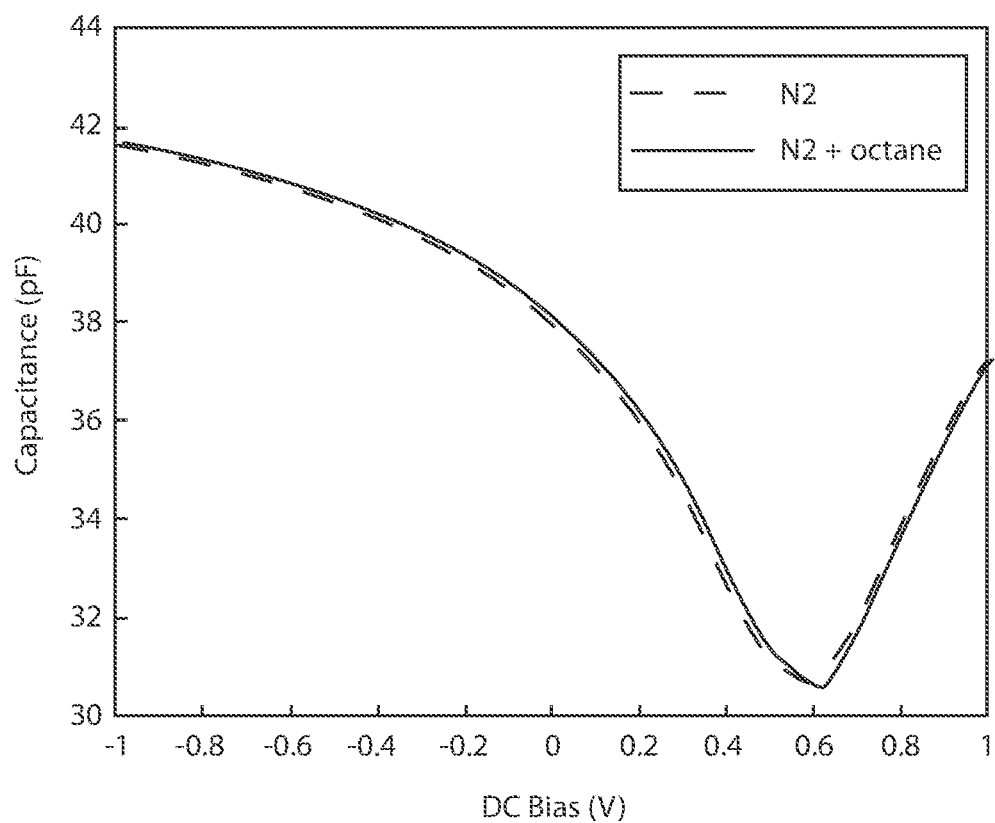
FIG. 11 is a graph showing capacitance versus DC bias voltage for a functionalized graphene varactor in response to octane binding in accordance with various embodiments herein.
Figure 12:
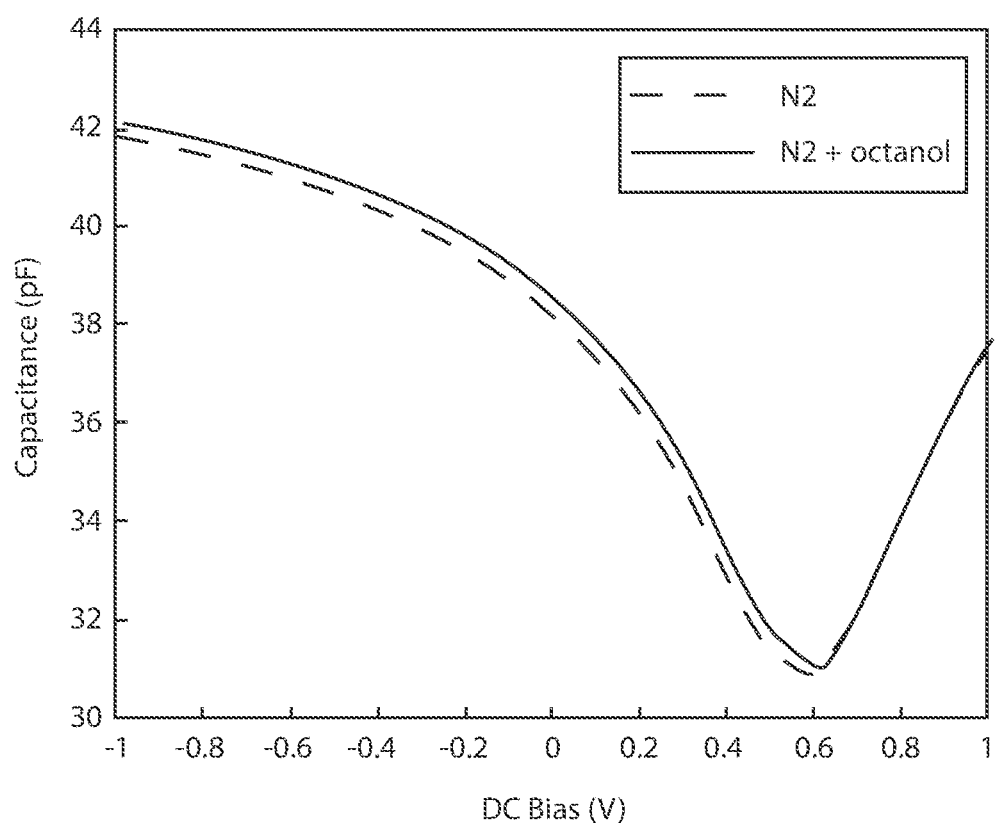
FIG. 12 is a graph showing capacitance versus DC bias voltage for a functionalized graphene varactor in response to octanol binding in accordance with various embodiments herein.

As shown in FIG. 10, it can be seen that binding of acetone caused the capacitance to voltage curve to shift sharply to the right, with the Dirac point increasing by approximately 0.1 volts. As shown in FIG. 11, it can be seen that binding of octane caused relatively small changes in the capacitance to voltage curve, but the shift to the right made the binding detectable. As shown in FIG. 12, it can be seen that binding of octanol caused relatively small changes in the capacitance to voltage curve, but the shift to the right made the binding detectable.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like. "Circuitry" can include both hardwired circuitry for execution of particular operations as well as processors that are programmed to execute instructions to provide the same functionality.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the scope to the precise forms disclosed herein. Rather, the embodiments are chosen and described so that others skilled in the art can appreciate and understand the principles and practices.

The invention claimed is:

1. A system for measuring analyte presence on a graphene varactor comprising:
   a capacitance to digital converter (CDC);
   a plurality of graphene varactors, each of the plurality of graphene varactors comprising
      an insulator layer,
      a gate electrode,
      a dielectric layer,
      a graphene layer, and
      a contact electrode; and
   a multiplexor configured to selectively provide electrical communication between the CDC and the plurality of graphene varactors;
   wherein the CDC is configured to measure the capacitance of the graphene varactor in response to an excitation signal over a plurality of DC bias voltages.

2. The system of claim 1, wherein an excitation signal is applied to a selected graphene varactor through the multiplexor.

3. The system of claim 1, the excitation signal comprising an alternating voltage.

4. The system of claim 1, wherein the amplitude of the excitation signal is fixed by the CDC.

5. The system of claim 1, further comprising a controller circuit configured to receive an electrical signal reflecting the capacitance of the graphene varactor.

6. The system of claim 5, the controller circuit comprising a microcontroller.

7. The system of claim 5, wherein the controller circuit is configured to calculate at least one parameter for the graphene varactor, the one parameter selected from the group consisting of
   maximum slope of capacitance to voltage;
   change in maximum slope of capacitance to voltage over a baseline value;
   minimum slope of capacitance to voltage;
   change in minimum slope of capacitance to voltage over a baseline value;
   minimum capacitance;
   change in minimum capacitance over a baseline value;
   voltage at minimum capacitance;
   change in voltage at minimum capacitance;
   maximum capacitance;
   change in maximum capacitance;
   ratio of maximum capacitance to minimum capacitance;
   response time constant; and
   ratios of any of the foregoing between the graphene varactor and a second graphene varactor.

8. The system of claim 1, further comprising an electronic component in electrical communication with the controller circuit and the CDC, the electronic component selected from the group consisting of an $I^2C$ or an SPI.

9. The system of claim 1, the graphene varactor comprising a functionalized graphene varactor.

10. The system of claim 1, wherein the plurality of graphene varactors are grounded.

11. The system of claim 1, wherein the plurality of graphene varactors are in electrical communication with an independent excitation output of the CDC.

12. The system of claim 1, further comprising one or more programmable digital to analog converters (DACs) in series with the plurality of graphene sensors.

13. The system of claim 1, further comprising a switch, the CDC in electrical communication with the switch and controlling the switch to selectively provide communication with output voltages of two programmable digital to analog converters (DACs), the programmed voltage difference between the DACs determining the excitation amplitude, and the difference between the programmed average voltage of the DACs and the bias at the CDC input determining the DC bias.

14. The system of claim 1, wherein a first graphene varactor of the plurality of graphene varactors is configured to detect a first volatile organic compound, wherein a second graphene varactor of the plurality of graphene varactors is configured to detect a second volatile organic compound, and wherein the first volatile organic compound is different from the second volatile organic compound.

15. A method for measuring analyte presence on a graphene varactor comprising:
   selectively providing electrical communication between a CDC and a plurality of graphene varactors using a multiplexor, each of the plurality of graphene varactors comprising
      an insulator layer,
      a gate electrode,
      a dielectric layer,
      a graphene layer, and
      a contact electrode;
   measuring a capacitance of each of the graphene varactors over a range of DC bias voltages; and
   determining one or more aspects for each varactor selected from the group consisting of:

maximum slope of capacitance to voltage;

change in maximum slope of capacitance to voltage over a baseline value;

minimum slope of capacitance to voltage;

change in minimum slope of capacitance to voltage over a baseline value;

minimum capacitance;

change in minimum capacitance over a baseline value;

voltage at minimum capacitance;

change in voltage at minimum capacitance;

maximum capacitance;

change in maximum capacitance;

ratio of maximum capacitance to minimum capacitance;

response time constant; and ratios of any of the foregoing between two different graphene sensors.

16. The method of claim 15, further comprising forming a capacitance to voltage curve from the measured capacitance of the graphene varactor over the range of DC bias voltages.

17. The method of claim 15, further comprising comparing the formed capacitance to voltage curve with a baseline capacitance to voltage curve.

18. The method of claim 17, further comprising distinguishing between different analytes binding to the graphene varactor.

19. The method of claim 15, wherein the range of DC bias voltages is from −3 V to 3 V.

* * * * *